(12) United States Patent
Small

(10) Patent No.: US 12,319,933 B2
(45) Date of Patent: Jun. 3, 2025

(54) SYSTEMS, METHODS, AND COMPOSITIONS FOR PRODUCTION OF CELLULAR AGRICULTURE PRODUCTS

(71) Applicant: ALCHEME BIO INC., Dover, DE (US)

(72) Inventor: Vanessa Small, San Diego, CA (US)

(73) Assignee: ALCHEME BIO INC., Dover, DE (US)

( * ) Notice: Subject to any disclaimer, the term of this patent is extended or adjusted under 35 U.S.C. 154(b) by 0 days.

(21) Appl. No.: 18/644,762

(22) Filed: Apr. 24, 2024

(65) Prior Publication Data

US 2024/0294868 A1    Sep. 5, 2024

Related U.S. Application Data

(63) Continuation of application No. PCT/US2024/025617, filed on Apr. 21, 2024.

(60) Provisional application No. 63/538,773, filed on Sep. 15, 2023, provisional application No. 63/461,095, filed on Apr. 21, 2023, provisional application No. 63/449,217, filed on Mar. 1, 2023.

(51) Int. Cl.
| | |
|---|---|
| *C12N 5/00* | (2006.01) |
| *G01N 30/86* | (2006.01) |
| *G01N 33/50* | (2006.01) |
| *G01N 30/02* | (2006.01) |

(52) U.S. Cl.
CPC ......... *C12N 5/0018* (2013.01); *C12N 5/0068* (2013.01); *G01N 30/8651* (2013.01); *G01N 33/5041* (2013.01); *G01N 33/5097* (2013.01); *G01N 2030/025* (2013.01); *G01N 2030/027* (2013.01)

(58) Field of Classification Search
CPC ........................... C12N 5/0018; C12N 5/0068
See application file for complete search history.

(56) References Cited

U.S. PATENT DOCUMENTS

| | | |
|---|---|---|
| 3,782,973 A | 1/1974 | Pittet et al. |
| 3,879,425 A | 4/1975 | Hall et al. |
| 4,011,233 A | 3/1977 | Dubs et al. |

(Continued)

OTHER PUBLICATIONS

Millipore Sigma (Citrate Buffer Concentrate) https://www.sigmaaldrich.com/US/en/product/mm/109884 (Year: 2024).*

(Continued)

*Primary Examiner* — James D Schultz
*Assistant Examiner* — Keenan A Bates
(74) *Attorney, Agent, or Firm* — Patrick IP Law; Christopher R. Patrick

(57) ABSTRACT

Culture supplement compositions for producing enhanced cellular agriculture products include a formulation including at least one enzyme in a carrier. As embodied herein, the formulation can be configured to adjust production of a base cellular agriculture product to produce an enhanced cellular agriculture product without reducing or inhibiting biomass production or cellular viability compared to the base cellular agriculture product. Furthermore, or as an alternative, the culture supplement composition can further include, in the carrier, at least one of a substrate or an additive. Cellular agriculture products made using the compositions are also provided.

19 Claims, 17 Drawing Sheets

(56) References Cited

U.S. PATENT DOCUMENTS

| | | | |
|---|---|---|---|
| 4,183,965 | A | 1/1980 | Mookherjee et al. |
| 4,386,106 | A | 5/1983 | Merritt et al. |
| 5,695,802 | A | 12/1997 | Van Den Ouweland et al. |
| 10,209,239 | B1 | 2/2019 | Hanson et al. |
| 10,296,718 | B2 | 5/2019 | Shibuya et al. |
| 2004/0191403 | A1 | 9/2004 | Hansen et al. |
| 2005/0227906 | A1 | 10/2005 | Schudel et al. |
| 2007/0161053 | A1 | 7/2007 | Li et al. |
| 2009/0053730 | A1 | 2/2009 | Adler et al. |
| 2009/0130282 | A1 | 5/2009 | Hofmann et al. |
| 2009/0215174 | A1 | 8/2009 | Zoller et al. |
| 2009/0221001 | A1 | 9/2009 | Zoller et al. |
| 2009/0270692 | A1 | 10/2009 | Hyde et al. |
| 2012/0204802 | A1* | 8/2012 | Nichols ............ A23K 20/158 119/230 |
| 2017/0242004 | A1 | 8/2017 | Hanson et al. |
| 2018/0143212 | A1 | 5/2018 | Giese et al. |
| 2018/0357205 | A1 | 12/2018 | Yamamoto |
| 2020/0245640 | A1* | 8/2020 | Clark ................ A23C 9/1526 |
| 2022/0007696 | A1 | 1/2022 | Lavon et al. |
| 2022/0061365 | A1 | 3/2022 | Vrljic et al. |
| 2022/0359044 | A1 | 11/2022 | Pappas et al. |

OTHER PUBLICATIONS

Calculator Academy W_W To W_V Calculator. https://calculator.academy/w-w-to-w-v-calculator/ (Year: 2024).*

American Pharmaceutical Review (Carrier Excipients). https://www.americanpharmaceuticalreview.com/pfu/7964385/soids/1402493/Excipient_Search/Carrier (Year: 2024).*

Soybean Oil Health Benefits. https://www.soyconnection.com/old-pages/soy-information-health-professionals/soybean-oil-for-health#:~:text=Soybean%20oil%20is%20primarily%20comprised,percent%20PUFA%20(table%201). (Year: 2022).*

Zeeb et al. Crosslinking of interfacial layers in multilayered oil-in-water emulsions using laccase: Characterization and pH-stability. Food Hydrocolloids 27: 126-136. (Year: 2012).*

El-Fakharany et al. Production and Application of Extracellular Laccase Produced by Fusarium oxysporum EMT. International Journal of Agriculture and Biology 18: 939-947. (Year: 2016).*

Chang et al. Integrated biocatalytic process for trehalose production and separation from rice hydrolysate using a bioreactor system. Food Chemistry 134: 1745-1753. (Year: 2012).*

Loster et al. Quantification of Cell-Matrix and Cell-Cell Adhesion Using Horseradish Peroxidase. Analytical Biochemistry 244: 96-102. (Year: 1997).*

Porstmann et al. Temperature Dependent Rise in Activity of Horseradish Peroxidase Caused By Non-Ionic Detergents and Its Use in Enzyme-Immunoassay. Clinica Chimica Acta 109: 175-181. (Year: 1981).*

Muniz-Mouro et al. Laccase Activity as an Essential Factor in the Oligomerization of Rutin. Catalysts 8: 1-15. (Year: 2018).*

Meissner et al. Development of a fixed bed bioreactor for the expansion of human hematopoietic progenitor cells. Cytotechnology 30: 227-234. (Year: 1999).*

McArthur et al. Cellular uptake and intracellular trafficking of long chain fatty acids. Journal of Lipid Research 40: 1371-1383. (Year: 1999).*

Devillers et al. Genome Sequence of the Oleaginous Yeast *Yarrowia lipolytica* H222. Microbiol Resour Announc 8: 1-2. (Year: 2019 ).*

U.S. Appl. No. 18/644,702, filed Apr. 24, 2024.

Abomohra, Abdelfatah, et al., "Enhancement of lipid extraction for improved biodiesel recovery from the biodiesel promising microalga Scenedesmus obliquus," *Energy Conversion and Management*. vol. 108, pp. 23-29, Jan. 2016.

Yuen Jr., John SK, et al., "Macroscale Adipose Tissue from Cellular Aggregates: A Simplified Method of Mass Producing Cell-Cultured Fat for Food Applications," bioRxiv, Jun. 18, 2022, available at https://doi.org/10.1101/2022.06.08.495192.

\* cited by examiner

106

400

SYSTEMS, METHODS, AND COMPOSITIONS FOR PRODUCTION OF CELLULAR AGRICULTURE PRODUCTS

CROSS-REFERENCE TO RELATED APPLICATIONS

This application is a continuation of International patent application no. PCT/US24/25617, filed Apr. 21, 2024, which claims priority to U.S. provisional application Nos. 63/449,217, filed Mar. 1, 2023, 63/461,095, filed Apr. 21, 2023, and 63/538,773, filed Sep. 15, 2023, each of which is incorporated by reference herein in its entirety.

BACKGROUND

Field

The disclosed subject matter relates to cellular agriculture products, including systems, methods, and compositions used for production of cellular agriculture products.

Description of Related Art

Cellular agriculture products generally refer to agricultural items, such as foods materials, or other products produced using cell cultures. This can include both acellular products and cellular products derived from cell cultures. Cellular agriculture products can provide several advantages over traditional agriculture products, including for example and without limitation, reduced environmental impact, lack of animal welfare concerns, increased product security, and enhanced product safety.

However, cellular agriculture products can lack desirable attributes compared to traditional agriculture products. For purpose of illustration and not limitation, cultivated foods, acellular and other cellular food products can lack desired flavors, nutritional values or texture identified with comparable traditional food products, and cultivated materials, acellular and other cellular material products can lack desired color, elasticity or texture identified with comparable traditional material products.

To overcome these deficiencies, producers of cellular agriculture products can apply additives to cells produced from cell cultures to improve less desirable attributes. Using flavor of cellular food products as an example, flavoring additives can be added to cells produced from a bioreactor or other cell production source to obtain a cellular food product having a flavor more closely resembling a comparable traditional food product. Yet such additive techniques can have disadvantages, including for example and not limitation, additional cost, greater production complexity, and longer or more complicated ingredient labels. Furthermore, additives can mask, but may not eliminate, undesirable attributes, and can be insufficient to replicate some desirable attributes, for example attributes for which no suitable additives exist.

Accordingly, there is an opportunity for cellular agriculture products having attributes that more closely align with consumer preferences, which can include emulating desirable attributes of a comparable traditional agriculture product. Such cellular agriculture products can be produced having desired attributes during the growth or expression phase, which can reduce or eliminate the use of additives added to cells to produce an end product.

Moreover, culture supplements can be used, for example and without limitation, for production of cellular agriculture products, such as for growing cells in a cell culture. Culture supplements can include, among other things, nutrients, growth factors, and other substances to support the growth and maintenance of cells. However, there is an opportunity for culture supplements suitable to produce cellular agriculture products having desired molecular attributes, such as molecular components affecting flavor, nutrition, color, elasticity, texture, and other desirable attributes of the cellular agriculture products.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the devices, methods and compositions particularly pointed out in the written description and claims hereof, as well as from the drawings.

To achieve these and other advantages and in accordance with the purpose of the disclosed subject matter, as embodied and broadly described, the disclosed subject matter includes a culture supplement composition for producing an enhanced cellular agriculture product, including a formulation including at least one enzyme in a carrier. As embodied herein, the formulation can be configured to adjust production of a base cellular agriculture product to produce an enhanced cellular agriculture product without reducing or inhibiting biomass production or cellular viability compared to the base cellular agriculture product. Furthermore, or as an alternative, the culture supplement composition can further include, in the carrier, at least one of a substrate or an additive.

Additionally or alternatively, as embodied herein, the carrier can include an emulsifier solution, powder, gel or solid substrate. Furthermore, or as an alternative, the emulsifier solution can include one or more of a nonionic detergent, a nonionic triblock copolymer, a nonionic surfactant, a poloxamer, or a zwitterionic detergent. In addition, or as a further alternative, the at least one enzyme can include one or more of a fatty acid desaturase, a cyclooxygenase, a lipoxygenase, an elongase, an oxidoreductase, a transferase, an endopeptidase, an exopeptidase, a hydrolase, a lyase, an isomerase, or a ligase. Moreover, or as an alternative, the at least one substrate can include one or more of a saturated fatty acid, a monounsaturated fatty acid, a polyunsaturated fatty acid, an omega-3 fatty acid, and an omega-6 fatty acid, a peptide, a protein, a nucleotide or an amino acid. As embodied herein, the at least one additive can include one or more of a growth factor protein, an insulin hormone, a peptide, or a transport protein.

Furthermore, or as an alternative, the at least one enzyme can have a concentration from 0.1% w/v to 3% w/v with enzymatic activity from 20000 to 20 units/mg. As embodied herein, the at least one substrate can have a concentration from 0.1 mM to 50 mM. Additionally or alternatively, as embodied herein, the at least one substrate can have a concentration from 0.1 mg/mL to 1 mg/mL. In addition, or as a further alternative, the carrier can have a concentration from 0.5% v/v to 5% v/v. As embodied herein, the formulation can be configured to be added to a cell culture medium of the base cellular agriculture product at a concentration from 1% v/v to 15% v/v. Moreover, as embodied herein, the formulation can be configured to modify at least one of a growth phase, an expression phase, a rehydration phase, or a structuring phase of the base cellular agriculture product in a production vessel.

According to other aspects of the disclosed subject matter, an enhanced cellular agriculture product can be made using the disclosed culture supplement compositions. Additionally or alternatively, as embodied herein, the enhanced cellular agriculture product can be made by adding one or more of the culture supplement compositions to a cell culture medium of the base cellular agriculture product at a concentration from 1% v/v to 15% v/v. Moreover, as embodied herein, the enhanced cellular agriculture product can have a similar cellular growth or cellular viability compared to the base cellular agriculture product.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the methods, systems and compositions of the disclosed subject matter. Together with the description, the drawings explain the principles of the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts.

DETAILED DESCRIPTION

Figure 1:
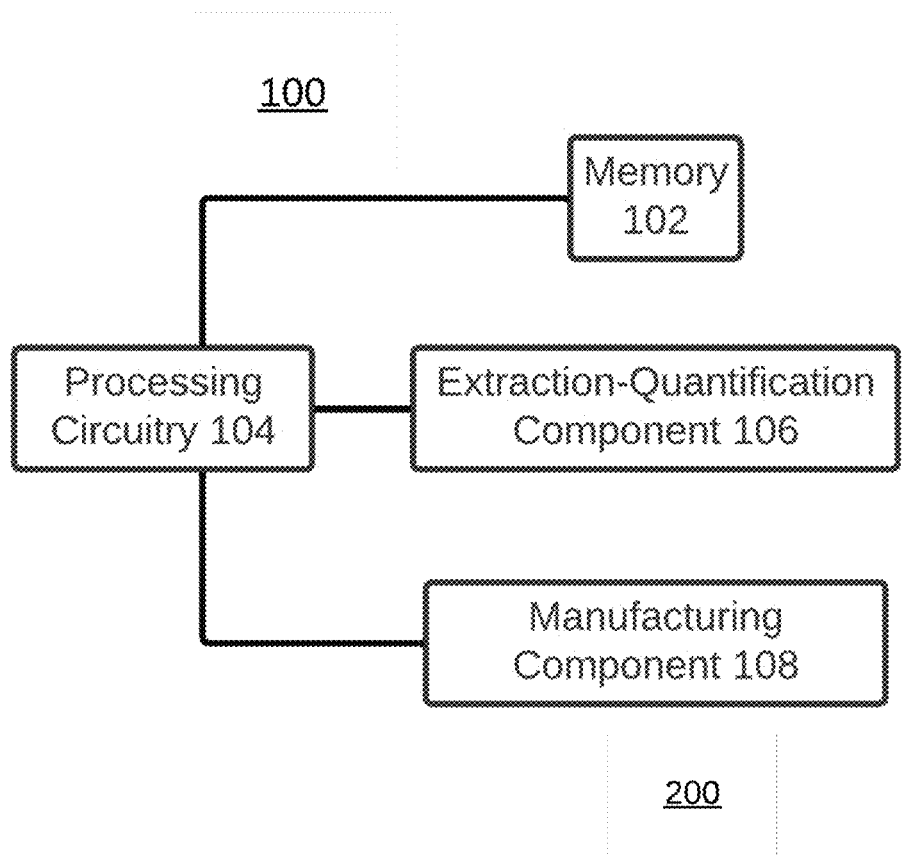
FIG. 1 is a diagram illustrating an exemplary system for cellular attribute alignment of a base cellular agriculture product with a reference product in accordance with the disclosed subject matter.

Reference will now be made in detail to the various aspects of the disclosed subject matter, exemplary embodiments of which are illustrated in the accompanying drawings. The structure and corresponding method of operation of the disclosed subject matter will be described in conjunction with the detailed description of the system.

The devices, methods and compositions presented herein may be used for production of cellular agriculture products, and are particularly suited for providing an enhanced cellular agriculture product by alignment of attributes of a base cellular agriculture product with a reference product.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of systems, methods and related compositions for production of cellular agriculture products in accordance with the disclosed subject matter are shown in FIGS. 1-13B. The systems, methods, and compositions described herein are suitable for producing cellular agriculture products having attributes that more closely align with consumer preferences, which can include desirable attributes of a comparable traditional agriculture product. Such cellular agriculture products, for purpose of illustration and not limitation, can be produced having desired attributes during the growth or expression phase, which can reduce or eliminate the use of additives added to cells to produce an end product.

Cellular agriculture products described herein are suitable for a variety of uses, including without limitation as food products (e.g., fats and lipids, meats, seafoods, dairy, eggs, cocoa, sweeteners, and substitutes for these), material products (e.g., textiles, silk, leather, paper products, and substitutes for these), and other commercial products (e.g., colors, dyes, and stains). Cellular agriculture products described herein can be produced various ways, including and without limitation by cultivation (e.g., by growing cells for biomass in a bioreactor), precision fermentation (e.g., by organisms producing proteins in a bioreactor), and plant-based processing (e.g., by growing plant cells processed to mimic a different product, such as products traditionally derived from animals, or by growing plant cells in a bioreactor). Cellular agriculture products described herein can have attributes aligned with a reference product as compared to a base cellular agriculture product. Such attributes can include attributes affected by the molecular composition of the cellular agriculture product, which can include for purpose of illustration and not limitation, flavor, nutrition, color, elasticity, or texture of the cellular agriculture product. For example and without limitation, systems, methods, and compositions disclosed herein are particularly suitable and beneficial for producing cellular food products, including cultivated foods, precision fermented foods and plant-based substitute foods.

In accordance with the disclosed subject matter herein, systems for cellular attribute alignment of a base cellular agriculture product with a reference product have at least one memory including, first data including a compositional profile of a reference product having a cellular attribute of interest, and second data including a compositional profile of a base cellular agriculture product produced to emulate the cellular attribute of interest of the reference product, and processing circuitry configured to identify, using the first data, one or more target compounds in the reference product affecting the attribute of interest, determine at least one compositional gap in the base cellular agriculture product compared to the reference product by comparison of compositional levels of the one or more target compounds in the first data to corresponding compositional levels of the one or more target compounds in the second data, and provide an adjustment to a manufacturing process or a manufacturing component for the base cellular agriculture product to reduce or eliminate the at least one compositional gap in the base cellular agriculture product affecting the attribute of interest to produce an enhanced cellular agriculture product.

According to other aspects of the disclosed subject matter, methods for cellular attribute alignment of a base cellular agriculture product with a reference product include accessing, using a processor, first data including a compositional profile of a reference product having a cellular attribute of interest, accessing, using the processor, second data including a compositional profile of a base cellular agriculture product produced to emulate the cellular attribute of interest of the reference product, identifying, using the processor and the first data, one or more target compounds in the reference product affecting the attribute of interest, determining, using the processor, at least one compositional gap in the base cellular agriculture product compared to the reference product by comparison of compositional levels of the one or more target compounds in the first data to corresponding compositional levels of the one or more target compounds in the second data, and providing, using the processor, an adjustment to a manufacturing process or a manufacturing component for the base cellular agriculture product to reduce or eliminate the at least one compositional gap in the base cellular agriculture product affecting the attribute of interest to produce an enhanced cellular agriculture product.

For purpose of illustration, and not limitation, reference is made to the exemplary embodiments of systems and methods for cellular attribute alignment of a base cellular agriculture product with a reference product shown in FIGS. 1-10C. As shown for example and without limitation in FIGS. 1 and 2, as embodied herein, a system 100 of FIG. 1 can be configured to perform method 200, for cellular attribute alignment of a base cellular agriculture product with a reference product.

For example and not limitation, as embodied herein, the base cellular agriculture product can include any cellular agriculture product described herein, including but not limited to, a cultivated food, a precision fermented food, a cultivated material product, another agricultural product produced from a cell culture, a plant-based cellular agriculture product, or a plant-based food substitute product (e.g., meat or dairy substitute). As embodied herein, the reference product can include any naturally-occurring or traditionally-produced product of interest to be emulated by a cellular agriculture product. For example and without limitation, the reference product can include an animal or plant-based food product, an animal or plant-based material product, or another naturally-occurring or traditionally-produced agricultural product. Each of the base cellular agriculture product and the reference product can have one or more cellular attributes of interest, which can include for example a flavor, a nutritional component or a nutritional value, a color, an elasticity, a texture, or any other attribute of interest affected by the molecular components of the product.

With reference to FIG. 1, as embodied herein, system 100 for cellular attribute alignment of a base cellular agriculture product with a reference product can include a memory 102 and a processing circuitry 104. As shown in FIG. 1, system 100 can further include an extraction-quantification component 106 in communication with processing circuitry 104. Additionally or alternatively, as embodied herein, system 100 can further include, or communicate with, a manufacturing component 108.

As embodied herein, memory 102 can include storage space for data or instructions accessible to processing circuitry 104. For example and without limitation, memory 102 can include one or more memories on a local device, including but not limited to random-access memory (RAM), read-only memory (ROM), flash memory, cache memory, secondary storage memory (e.g., hard disk drive (HDD) or solid-state drive (SSD)), or can be distributed across a plurality of devices, such as one or more cloud storage devices or other remote storage devices accessible over a network.

Moreover, as embodied herein, memory 102 can store, for example, first data including a compositional profile of a reference product having a cellular attribute of interest, and second data including a compositional profile of a base cellular agriculture product produced to emulate the cellular attribute of interest of the reference product. Additionally or alternatively, as embodied herein, memory 102 can include a plurality of sets of first data including compositional profiles of a plurality of reference products having one or more cellular attributes of interest, and a plurality of sets of second data including compositional profiles of a plurality of base cellular agriculture products produced to emulate the one or more cellular attributes of interest.

Further, as embodied herein, memory 102 can store compositional profiles and other data, including for example and without limitation, data that can be used by processing circuitry 104 to identify one or more cellular attributes of interest. As embodied herein, data stored by memory 102 can include information identifying particular molecular components affecting the one or more cellular attributes of interest as described herein. Memory 102 can further include compositional profiles and other data obtained from third-party databases or research, including publicly-available databases or research, prior samples and analysis of cellular agriculture products compared to reference products, data obtained from external devices and sensors, including but not limited to electronic tongues or electronic noses, data obtained from flavor panels, and data relating consumer preferences to reference products or to attributes of interest.

For purpose of illustration only, and not limitation, the cellular agriculture products and reference products can be food products, and the cellular attributes of interest can be related to flavor, nutrition, texture or color of the food products. As embodied herein, using flavor as an example, the compositional profiles of the base cellular agriculture product and the reference product each can include a measurement of one or more molecular flavor components, including but not limited to free fatty acids, nucleotides (including ribonucelotides), kokumi or umami peptides.

Additionally or alternatively, as embodied herein, the compositional profiles can include measurements or data obtained from cellular agriculture products or reference products using various forms of spectroscopic analysis, such as nuclear magnetic resonance (NMR) spectroscopy, infrared (IR) spectroscopy, or mass spectrometry. The resulting data can provide detailed information about the molecular structure and composition of the cellular agriculture products and reference products. Moreover, or as an alternative, the compositional profiles from such analyses can be stored in one or more records or databases in memory 102. In addition, or as a further alternative, the compositional profiles can be obtained using extraction-quantification component 106, as described herein.

Referring still to FIG. 1, processing circuitry 104 can include one or more processors configured to perform data processing and control functions described herein. For example and without limitation, processing circuitry 104 can be configured to implement any of the methods and interact with any of the systems or components shown or described with respect to FIGS. 2-10C. Processing circuitry 104 can include local processing circuitry, such as one or more processors disposed entirely on a mobile device, computer workstation, or laboratory instrument, or remote processing circuitry, such as a remote processor in a smartphone, smart glasses, smart watch, or other remote device, or any combination thereof. Other suitable configurations of processing circuitry 104 are envisioned. As an example, processing circuitry 104 of system 100 can include or be implemented as a special-purpose processor, such as an application-specific integrated circuit (ASIC) or a field programmable gate array (FPGA). As embodied herein, processing circuitry 104 can include a general-purpose processing unit (e.g., a central processing unit (CPU)), or can include another programmable processor that is temporarily configured by software to execute the functions of system 100. More generally, processing circuitry 104 can be implemented using hardware, firmware, software, or a suitable combination of hardware, firmware, and software.

Processing circuitry 104 can further include a user interface to provide feedback and information, such as reports, to a user and allow for selection of operation of system 100, for example and without limitation, to control or adjust operation of system 100, including extraction-quantification component 106 or manufacturing component 108, each if provided or in communication with system 100. The user interface can include, for example and without limitation, a touch-screen display, microphone, or other input device, which can be disposed entirely on system 100, or can be entirely or at least partially remote, such as by using a touch-screen display, microphone or other input device of the smartphone, smart glasses, smart watch, or other remote device for example when used as a remote component of processing circuitry 104.

Referring still to FIG. 1, additionally or alternatively, system 100 can further include, or communicate with using processing circuitry 104, one or more extraction-quantification components 106 configured to extract and quantify analytical samples of cellular agriculture products and reference products, as shown and described herein. For purpose of illustration and not limitation, as embodied herein, extraction-quantification component 106, if provided, can include a chromatographic and/or a spectroscopic analyzer, such as one or more of a gas chromatograph, a mass spectrometer, and a liquid chromatograph, as part of or in communication with system 100. Extraction-quantification component 106 can include any additional features described herein, including without limitation as shown and described with respect to FIGS. 3-4.

With configured reference to FIG. 1, furthermore, or as an alternative, system 100 can further include, or communicate with using processing circuitry 104, one or more manufacturing components 108 for producing cellular agriculture products. For purpose of illustration and not limitation, as embodied herein, manufacturing component 108 can include a bioreactor to grow or express cells used for cellular agriculture products. Manufacturing component 108 can include any additional features described herein, including without limitation as shown and described with respect to FIGS. 2, 9 and 10A-10C.

Figure 2:
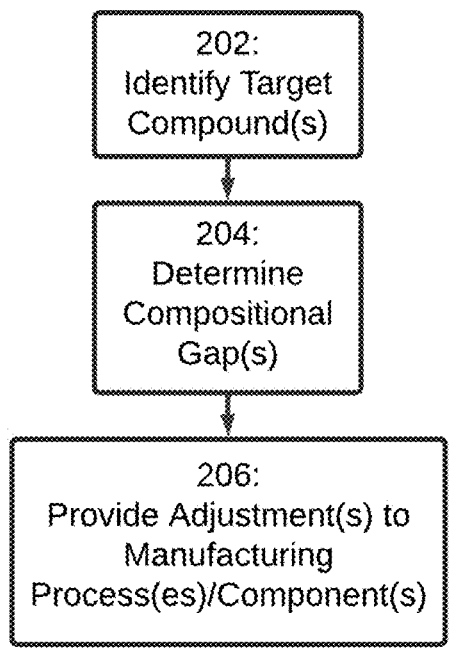
FIG. 2 is a diagram illustrating an exemplary technique for cellular attribute alignment of a base cellular agriculture product with a reference product in accordance with the disclosed subject matter.

Referring now to FIG. 2, as embodied herein, system 100 can be configured to perform method 200 for cellular attribute alignment of a base cellular agriculture product with a reference product. For purpose of illustration and not limitation, as embodied herein, at 202, processing circuitry 104 can be configured to identify, using the first data in memory 102, one or more target compounds in the reference product affecting the attribute of interest. The one or more target compounds can be identified, for example, by examination of compositional profiles of one or more reference products having the attribute of interest. The one or more reference products can be identified from a variety of data sources, for example and without limitation, by third-party databases or research, data obtained from flavor panels, and data connecting consumer preferences to attributes of interest. As embodied herein, the compositional profiles of the one or more identified reference products can be examined, for example and without limitation, by comparing one or more identified compounds in the reference product to a threshold. For example, as embodied herein, one or more identified compounds in the reference product exceeding a size or a volume threshold determined from the compositional profile data can be identified as affecting the attribute of interest in the reference product.

Referring still to FIG. 2, as embodied herein, at 204, processing circuitry 104 can be configured to determine at least one compositional gap in the base cellular agriculture product compared to the reference product by comparison of compositional levels of the one or more target compounds in the first data to corresponding compositional levels of the one or more target compounds in the second data. For purpose of illustration and not limitation, as embodied herein, the first data and second data obtained as described herein can be analyzed to identify differences in the compositional levels of the target compounds between the base cellular agriculture product and the reference product. Such analysis can involve, for example and without limitation, comparing chemical shifts in NMR spectra, absorption bands in IR spectra, or mass-to-charge ratios in mass spectrometry data.

With continued reference to FIG. 2, as embodied herein, at 206, processing circuitry 104 can be configured to provide an adjustment to a manufacturing process or a manufacturing component 108 for the base cellular agriculture product. The adjustment can reduce or eliminate the at least one compositional gap in the base cellular agriculture product affecting the attribute of interest to produce an enhanced cellular agriculture product.

As embodied herein, the adjustment to the manufacturing process or the manufacturing component can be configured such that the adjustment does not reduce or inhibit cellular growth or cellular viability of the enhanced cellular agriculture product compared to the base cellular agriculture product. For example and not limitation, the adjustment to the manufacturing process or the manufacturing component can be configured to modify a growth phase or an expression phase of the base cellular agriculture product, as embodied herein, in a bioreactor.

Additionally or alternatively, as embodied herein, processing circuitry 104 can be configured to provide the adjustment by formulating a target product to measure alignment or quality control of the enhanced cellular agriculture product compared to the reference product or to a target reference standard. That is, the target product can be formulated by the processing circuitry 104 to provide a quality control target or reference standard for the enhanced cellular agriculture product derived from reducing or eliminating the at least one compositional gap of the base cellular agriculture product determined in 204. The target product can thus be used to adjust a manufacturing process or manufacturing component 108 of the base cellular agriculture product to obtain the target product representing the enhanced cellular agriculture product having increased alignment with the attribute of interest of the reference product or the target reference standard. Moreover, processing circuitry 104 can be further configured to control operation of a manufacturing component, such as a mixer, to combine the formulation components to produce the formulated target product. For example and without limitation, as embodied herein, each component identified as relevant to an attribute of interest can be mixed by the mixer at a specified concentration and dissolved in a solvent to create a standard used for instrument calibration and compared to a library of known compounds (e.g., from MassHunter software by Agilent).

Furthermore, or as an alternative, as embodied herein, processing circuitry 104 can be configured to provide the adjustment to the manufacturing process or the manufacturing component by formulating a culture supplement composition used to produce cells of the enhanced cellular agriculture product. That is, the culture supplement composition, which can include for purpose of illustration and not limitation any features of culture supplement composition 1000 described further herein, can be added during manufacture of the base cellular agriculture product, for example and without limitation during at least one of a growth phase, an expression phase, a rehydration phase, or a structuring phase of the base cellular agriculture product. As embodied herein, the culture supplement composition can be added to growth media of the base cellular agriculture product. For example and not limitation, manufacturing component 108 can include a production vessel, such as a bioreactor, a shake flask, or other vessel suitable for biomass production, and a mixer. As embodied herein, processing circuitry 104 can be further configured to control operation of at least one of the production vessel or the mixer, to produce the formulated culture supplement composition or apply the culture supplement composition to the cell culture in the production vessel.

An enhanced cellular agriculture product can thus be formed having an increased alignment of the attribute of interest with the reference product. As such, the reference product can be selected to be used as a proxy for alignment with consumer preferences, and the enhanced cellular agriculture product can thus have increased alignment of the attribute of interest with consumer preferences in the market.

Figure 3:
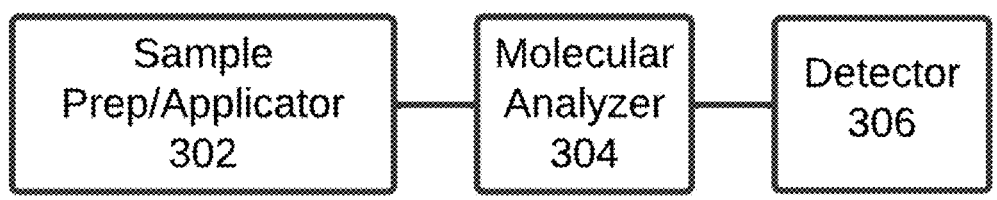
FIG. 3 is a diagram illustrating an exemplary extraction and quantification component for the system of FIG. 1 in accordance with the disclosed subject matter.
Figure 4:
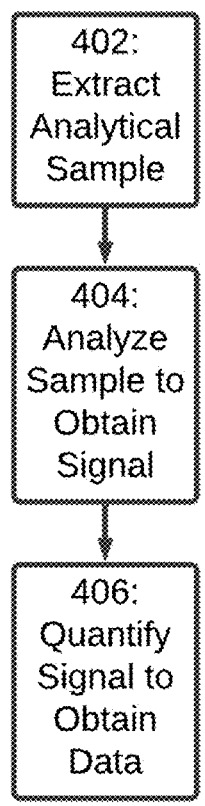
FIG. 4 is a diagram illustrating an exemplary technique for cellular attribute alignment of a base cellular agriculture product using the exemplary extraction and quantification component of FIG. 3.

Additional details and examples of system 100 and method 200 for producing an enhanced cellular agriculture product are shown and described, for purpose of illustration and confirmation of the disclosed subject matter and not limitation, with reference to the exemplary embodiments of FIGS. 3-10C. Referring now to FIGS. 3 and 4, as embodied herein, an exemplary extraction-quantification component 106 can be configured to perform method 400 for extraction and quantification of a sample to obtain data, which can include compositional profile data as described herein.

With reference to FIGS. 3 and 4, extraction-quantification component 106 can include a sample preparator/applicator 302, molecular analyzer 304, and detector 306, which can be arranged together for example as part of a unitary device, or separately as separate devices or components, such as in a local workstation with, or in a remote workstation from, processing circuitry 104 of system 100.

For example and not limitation, as embodied herein, sample preparator/applicator 302 can include filters, centrifuges, chromatographs, or any other sample preparation and application components used to separate components of interest from other materials in samples obtained of base cellular agriculture products or reference products to obtain an analytical sample. Sample preparator/applicator 302 can thus be configured to extract, at 402, an analytical sample of the base cellular agriculture product. For example and without limitation, sample preparator/applicator 302 can be configured to apply an extraction solution to a sample of the base cellular agriculture product to obtain the analytical sample. As embodied herein, the analytical sample can thus be obtained from less than 2 grams of the base cellular agriculture product. Additionally or alternatively, as embodied herein, the extraction and analysis of the analytical sample can thus be performed without substantially altering the emulated cellular attribute of interest of the base cellular agriculture product. That is, using flavor as an example only and without limitation, the extraction solution can be applied without substantially altering the flavor of the base cellular agriculture product being analyzed, which can provide a more accurate analysis compared to other techniques, the use of which can alter the flavor of the base cellular agriculture product.

Referring still to FIGS. 3 and 4, extraction-quantification component 106 can include a molecular analyzer 304. Molecular analyzer 304 can include a chromatographic and/or a spectroscopic analyzer, such as one or more of a gas chromatograph, a mass spectrometer, a liquid chromatograph, or an infrared spectroscope. Molecular analyzer 304 can be configured to analyze, at 404, the analytical sample and provide a signal indicative of one or more analytes of interest.

With continued reference to FIGS. 3 and 4, extraction-quantification component 106 can include a detector 306, which can be a part of or separate from molecular analyzer 304. Detector 306 can include, for example and without limitation a photodiode detector or other spectrum detector. As embodied herein, detector 306 can be further implemented, in whole or in part, by processing circuitry 104. Detector 306 can be configured to quantify, at 406, the signal indicative of the one or more analytes of interest to provide the data, including compositional profile data.

Using cellular agriculture food products by way of example only and not limitation, attributes affecting flavor can be analyzed using the systems and methods of the disclosed subject matter. For purpose of illustration only and not limitation, the disclosed subject matter can be useful for analyzing fats, oils and lipids from cultured seafood, cultured animal-derived products, plant-based products or other precision fermentation-derived products. For example and not limitation, extraction-quantification component 106 can be used for extracting and quantifying cultured fats for free fatty acid flavor profile constituents.

In some embodiments, gas chromatography (GC) and mass spectrometry (MS) can be used to obtain data in accordance with the disclosed subject matter. Additionally or alternatively, in this example, systems and techniques for sample extraction and preparation are provided to allow for analysis using high-performance liquid chromatography (HPLC), for example to analyze free fatty acids in cultured fats, lipids and oil products.

In this example, extraction-quantification component 106 can be configured to quantify flavor constituents of cultured fats, lipids, oils and other products. This example involves the use of free fatty acid and free fatty acid reference standards to identify and determine the concentration of at least one free fatty acid and/or at least one free fatty acid in a sample of cultured fats, lipids or oil. As embodied herein, the extraction-quantification component 106 disclosed herein can allow for analysis of the sample with a sample size of less than 2 grams. Extraction-quantification component 106 can be used to perform accurate analysis while avoiding or mitigating sample loss or contamination. Furthermore, extraction-quantification component 106 can be used to perform analysis of the sample without the need for additional processing steps that could alter the flavor constituents of the cultured fat, which can provide a more reliable and accurate analysis compared to conventional systems and techniques.

Extraction-quantification component 106 can be configured to perform enzymatic hydrolysis of a cultured fat, lipid or oil sample, as embodied herein, using a lipase before the extraction of fatty acids produced from a sample of cultured fat tissue in an extraction solution with a solvent to obtain an analytical sample. The analytical sample can be diluted in a dilution solution. The analytical sample can be subjected to chromatographic separation and detected with a detector. The concentration of at least one free fatty acid and/or at least one free fatty acid in the sample of cultured fats can then be determined. Thus, in this example, as embodied herein, extraction-quantification component 106 can be configured to perform enzymatic hydrolysis of the sample prior to extraction and sample analysis.

As embodied herein, extraction-quantification component 106 can include a homogenizer to extract free fatty acids from the sample of cultured fat cells. Additionally or alternatively, the free fatty acids can be extracted using an extraction solution with a solvent, such as ethanol, methanol, dichloromethane, n-heptane, acetonitrile, formic acid, acetic acid, triethanolamine, or trichloroacetic acid in water.

Furthermore, or as an alternative, both the extraction solution and the dilution solution can include an internal reference standard with a known response ratio relative to the at least one free fatty acid in the detector. Moreover, as embodied herein, the dilution solution can further include a second standard with a known response ratio in the detector.

Extraction-quantification component 106 thus can analyze the flavor constituents of cultured fat, lipid, and oil applications using a small amount of sample, e.g., less than 2 grams. Extraction-quantification component 106 can be configured to perform enzymatic hydrolysis of the cultured, fat, lipid, or oil sample, and extract the cultured fat, lipid, or oil sample in an extraction solution. Extraction-quantification component 106 can thus produce an analytical extract including the free fatty acids and free fatty acids dissolved in the extraction solution. The extraction solution, as embodied herein, can include a solvent, an internal standard, which can include a saturated fatty acid, such as myristic acid or lauric acid, and a second external standard, which can include a free fatty acid panel.

Additionally or alternatively, as embodied herein, extraction-quantification component 106 can be configured to perform HPLC analysis. For example, molecular detector 304 can include a high-performance liquid chromatograph. At 402, HPLC analysis of the analytical extract can produce a signal for at least one free fatty acid and at least one free fatty acid, and can produce a signal for each of the standards. The signal for the at least one free fatty acid can be normalized based on the signal from the internal standard to quantify the at least one free fatty acid in the test sample. As embodied herein, the first internal standard can be a saturated fatty acid, such as myristic acid or lauric acid, at a known concentration. Moreover, as embodied herein, the concentrations of individual fatty acids can be determined using a calibration curve of a free fatty acids standard.

Figure 5A:
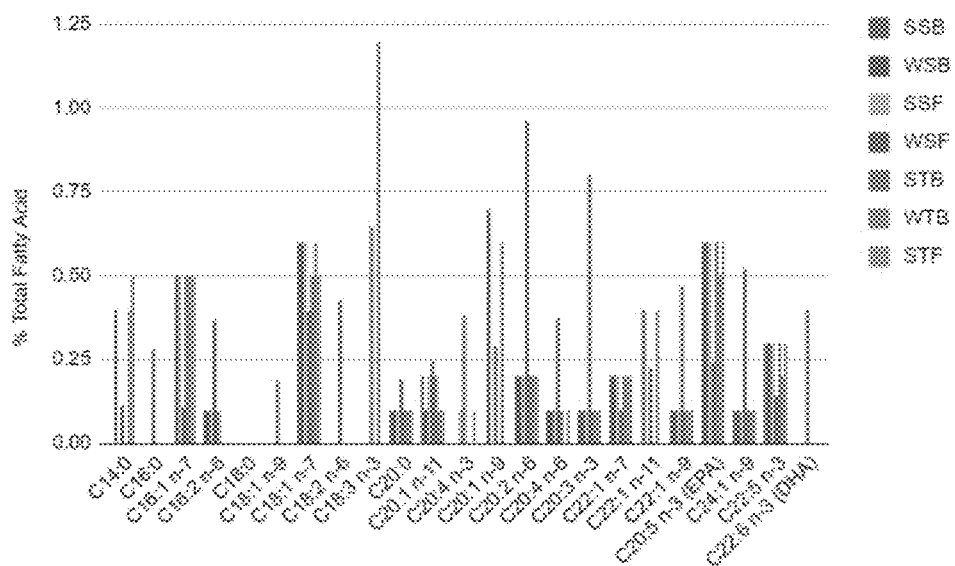
FIG. 5A is a graph illustrating exemplary embodiments of compositional profiles of reference products in accordance with the disclosed subject matter.
Figure 5B:
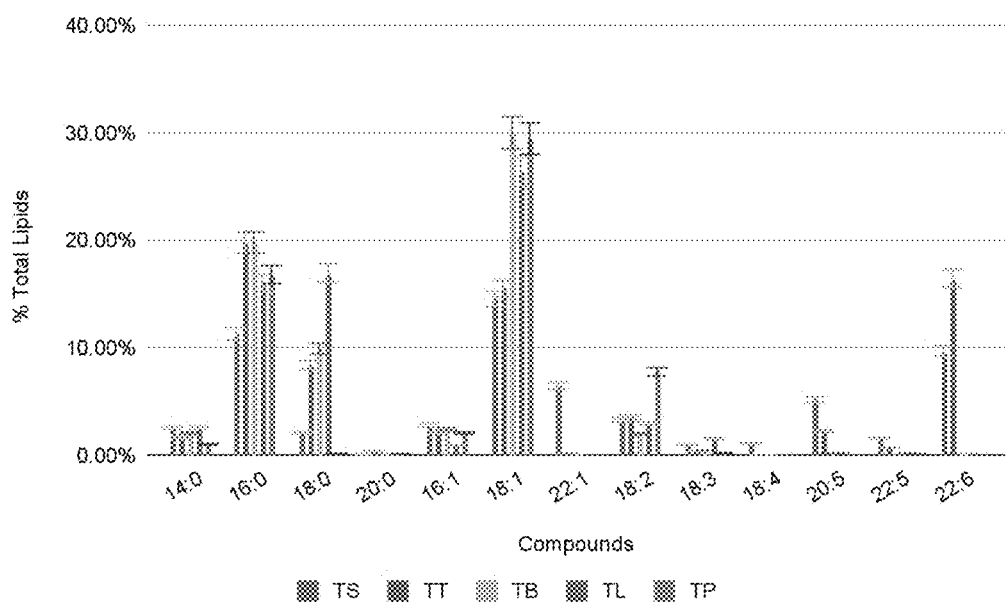
FIG. 5B is a graph illustrating exemplary embodiments of compositional profiles of reference products in accordance with the disclosed subject matter.

With reference to FIGS. 5A and 5B, exemplary compositional profiles of analytical samples of reference products, embodied herein as animal-based meat and seafood products, obtained from HPLC analysis are shown. FIG. 5A shows free fatty acids present in traditional seafood and animal fat products, including Summer Salmon Body (SSB), Winter Salmon Body (WSB), Summer Salmon Filet (SSF), Winter Salmon Fillet (WSF), Summer Trout Body (STB), Winter Trout Body (WTB), and Summer Trout Fillet (STF). FIG. 5B shows free fatty acids present in traditional seafood and animal fat products, including Traditional Salmon (TS), Traditional Tuna (TT), Traditional Beef (TB), Traditional Lamb (TL), and Traditional Pork (TP). For purpose of illustration and not limitation, peaks were identified by retention times in comparison to the free fatty acids standards. Thus, extraction-quantification component 106 can include a molecule detector 304 configured to perform at least one chromatographic separation, such as HPLC. Additionally or alternatively, as embodied herein, extraction-component 106 can include at least one detector 306 including a photodiode array detector to detect a visual signal from the molecular detector 304.

As embodied herein, at least one free fatty acid detected by extraction-quantification component 106 can be selected from the group consisting of saturated fatty acids, monounsaturated fatty acids and polyunsaturated fatty acids. As embodied herein, extraction-quantification component 106 can include sample preparator/applicator 302 having a solvent including ethanol, methanol, dichloromethane, n-heptane, acetonitrile, formic acid, acetic acid, triethanolamine, or trichloroacetic acid in water.

Additionally or alternatively, as embodied herein, extraction-quantification component 106 can perform extraction of free fatty acids from the sample of cultured fats cells, for example using a homogenizer. The free fatty acids can be extracted using an extraction solution with a solvent, such as ethanol, methanol, dichloromethane, n-heptane, acetonitrile, formic acid, acetic acid, triethanolamine, or trichloroacetic acid in water.

Furthermore, or as an alternative, exemplary extraction-quantification component 106 can perform enzymatic hydrolysis of a cultured fat, lipid or oil sample, for example and as embodied herein, using a lipase prior to extraction of fatty acids produced from a sample of cultured fat tissue in an extraction solution with a solvent to obtain an analytical sample. The analytical sample can be diluted in a dilution solution.

Moreover, as embodied herein, the analytical sample can be subjected to chromatographic separation and detected with a detector. The concentration of at least one free fatty acid and/or at least one free fatty acid in the sample of cultured fat, lipid or oil sample can be determined from the detector output to produce the compositional profile from the analytical sample.

As embodied herein, both the extraction solution and the dilution solution can include a first reference standard with a known response ratio relative to the at least one free fatty acid in the detector, and an external reference standard with a known response ratio relative to the at least one free fatty acid in the detector. Additionally or alternatively, as embodied herein, the external standard can include a free fatty acid panel including one or more of the following: myristic acid, palmitic acid, palmitoleic acid, hexadecadienoic acid, stearic acid, oleic acid, linoleic acid, alpha-linolenic acid, arachidic acid, gadoleic acid; cis-9-eicosenoic acid, eicosatetraenoic acid, eicosenoic acid, arachidonic acid, eicosatrienoic acid, erucic acid, cetoleic acid, docosenoic acid, eicosapentaenoic acid (EPA), nervonic acid, docosapentaenoic acid (DPA), and docosahexaenoic acid (DHA).

By way of another example, for purpose of illustration only and not limitation, other attributes affecting flavor can be analyzed using the systems and methods of the disclosed subject matter. For example and without limitation, the disclosed subject matter can be useful for analyzing cultivated meat, cultivated seafood, precision fermented products, plant-based products, and other cultured animal-derived products. As embodied herein, for example and not limitation, extraction-quantification component 106 can be used for extracting and quantifying cultivated meat umami peptide flavor profile constituents. Extraction-quantification component 106 can thus be configured for analysis and measurement of cultivated meat secondary compounds imparting umami flavor, including nucleotides, amino acids, and kokumi or umami peptides.

As embodied herein, umami taste can be desirable, for example and without limitation, for food seasoning and healthy eating. Umami substances can include, for example and without limitation, monosodium glutamate, nucleotides, and peptides.

In this example, extraction-quantification component 106 can be configured to extract and quantify the flavor constituents of cultivated meat and other applications. As embodied herein, extraction-quantification component 106 can use nucleotide, kokumi and umami peptide reference standards to identify and determine the concentration of at least one nucleotide and/or at least one kokumi or umami peptide in a sample of cultivated meat tissue. Moreover, as embodied herein, extraction-quantification component 106 can allow for analysis of the sample with a sample size of less than 2 grams. Thus, extraction-quantification component 106 used to perform accurate analysis while avoiding or mitigating sample loss or contamination. Furthermore, extraction-quantification component 106 can be used to perform analysis of the sample without additional or alternative processing steps that could alter the kokumi or umami flavor constituents of the cultivated meat, which can provide a more reliable and accurate analysis compared to conventional systems and techniques.

As embodied herein, extraction-quantification component 106 can include a homogenizer to extract kokumi or umami peptides from the sample of cultivated meat tissue. Additionally or alternatively, the kokumi or umami peptides can be extracted using an extraction solution with a solvent, such as ethanol, methanol, acetonitrile, formic acid, acetic acid, triethanolamine, or trichloroacetic acid in water. Furthermore, or as an alternative, as embodied herein, the sample can be frozen in liquid nitrogen before homogenizing the sample of cultivated meat tissue in an extraction solution with a cell homogenizer to obtain an analytical sample. The analytical sample can be diluted in a dilution solution as described herein. The analytical sample can be subjected to chromatographic separation, and detected with a detector, as described herein. The concentration of at least one nucleotide and/or at least one kokumi or umami peptide in the sample of cultivated meat can be determined from the detector output.

In addition, or as a further alternative, both the extraction solution and the dilution solution can include a first reference standard with a known response ratio relative to the at least one nucleotide in the detector, and a second reference standard with a known response ratio relative to the at least one kokumi or umami peptide in the detector. Additionally, as embodied herein, the dilution solution can further include a third standard with a known response ratio in the detector.

Extraction-quantification component 106 thus can analyze the kokumi or umami flavor constituents of cultivated meat and other products using a small amount of sample, e.g., less than 2 grams. Extraction-quantification component 106 can be configured to extract the cultivated meat test sample in an extraction solution, thereby producing an analytical extract including the nucleotides, kokumi and umami peptides of the sample dissolved in the extraction solution. For example and as embodied herein, the extraction solution can include a solvent, a first internal standard including a nucleotide, such as adenosine triphosphate (ATP), and a second reference standard including a kokumi or an umami peptide panel.

Additionally or alternatively, as embodied herein, extraction-quantification component 106 can be configured to perform HPLC analysis. For example, molecular detector 304 can include a liquid chromatograph. At 402, HPLC analysis of the analytical extract can produce a signal for at least one nucleotide and at least one kokumi or umami peptide, and can produce a signal for each of the standards. The signal for the at least one nucleotide can be normalized based on the signal from the first internal standard to quantify at least one nucleotide in the test sample. As embodied herein, the signal for the at least one kokumi or umami peptide can be normalized based on the signal from the second reference standard to quantify the at least one kokumi or umami peptide in the test sample. Additionally or alternatively, as embodied herein, the first internal standard can include a nucleotide, such as ATP, at a known concentration, and the second internal standard can include a di-peptide such as Glu-Leu, at a known concentration.

Extraction-quantification component 106 can include a molecule detector 304 configured to perform at least one chromatographic separation, such as HPLC. Additionally or alternatively, as embodied herein, extraction-component 106 can include at least one detector 306 including a photodiode array detector to detect a visual signal from the molecular detector 304.

As embodied herein, at least one nucleotide can be selected from adenosine monophosphate (AMP), adenosine diphosphate (ADP), adenosine triphosphate (ATP), Inosine-5-monophosphate (IMP), Hypoxanthine, Disodium guanosine 5-monophosphate (GMP), guanosine monophosphate (GMP), guanosine diphosphate (GDP), guanosine triphosphate (GTP), cytidine monophosphate (CMP), cytidine diphosphate (CDP), cytidine triphosphate (CTP), uridine monophosphate (UMP), uridine diphosphate (UDP), and uridine triphosphate (UTP).

Additionally or alternatively, as embodied herein, at least one kokumi or umami peptide can be selected from dipeptides, tripeptides, tetrapeptide, pentapeptides, hexapeptides, heptapeptides, octapeptides, and undecapeptides.

Furthermore, or as an alternative, as embodied herein, the solvent can include ethanol, methanol, acetonitrile, formic acid, acetic acid, triethanolamine, or trichloroacetic acid in water.

Figure 6A:
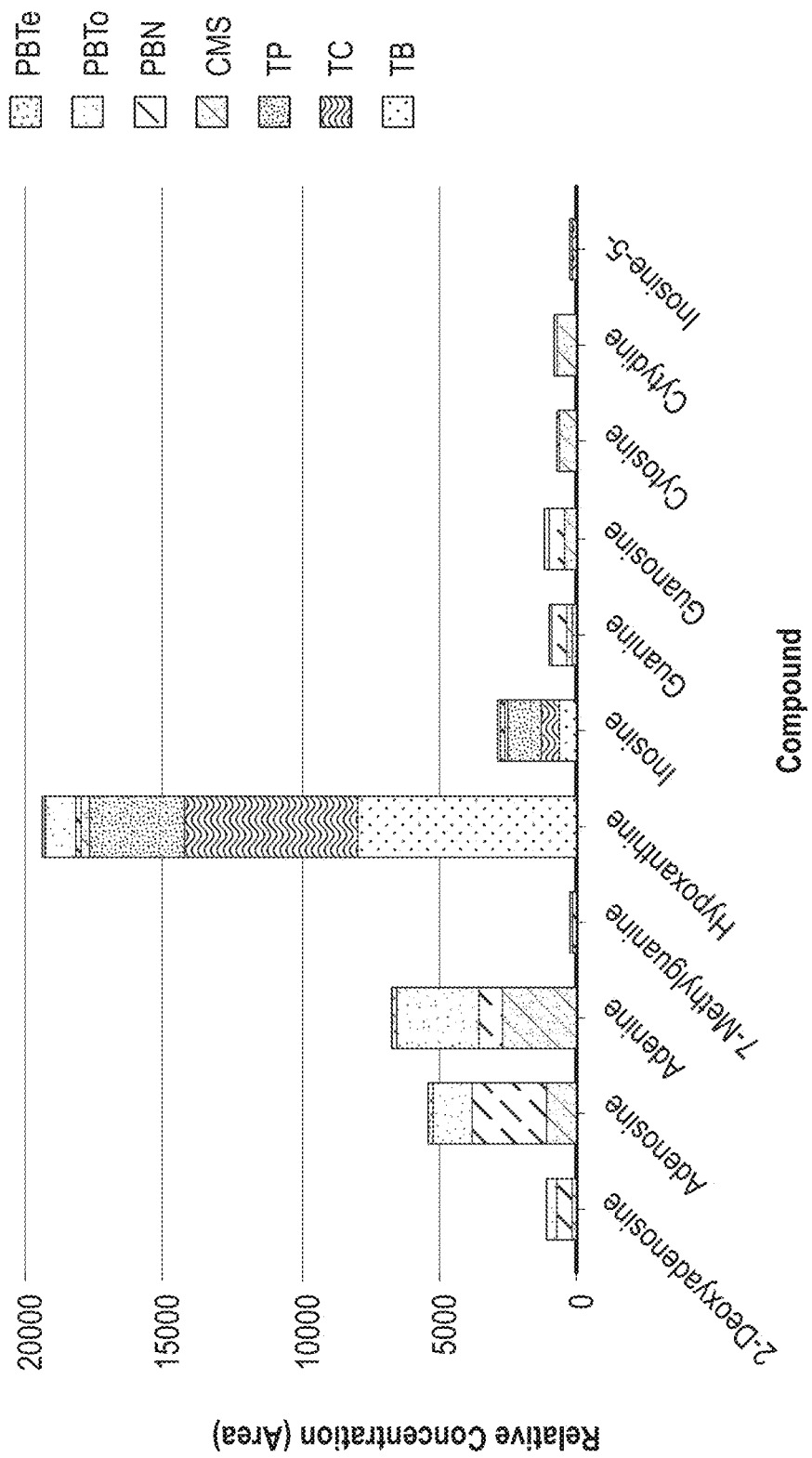
FIG. 6A is a graph illustrating alternative embodiments of compositional profiles of reference products and base cellular agriculture products, shown side-by-side for purpose of illustration and comparison.

With reference to FIG. 6A, as embodied herein, compositional profiles of nucleotides of traditional meat products and meat substitute products are shown for purpose of illustration, including Plant-based tofu (PBTo), Plant-based tempeh (PBTe), Plant-based natto (PBN), Cultivated Meat Substitutes (CMS), Traditional Pork (TP), Traditional Chicken (TC), and Traditional Beef (TB).

Figure 6B:
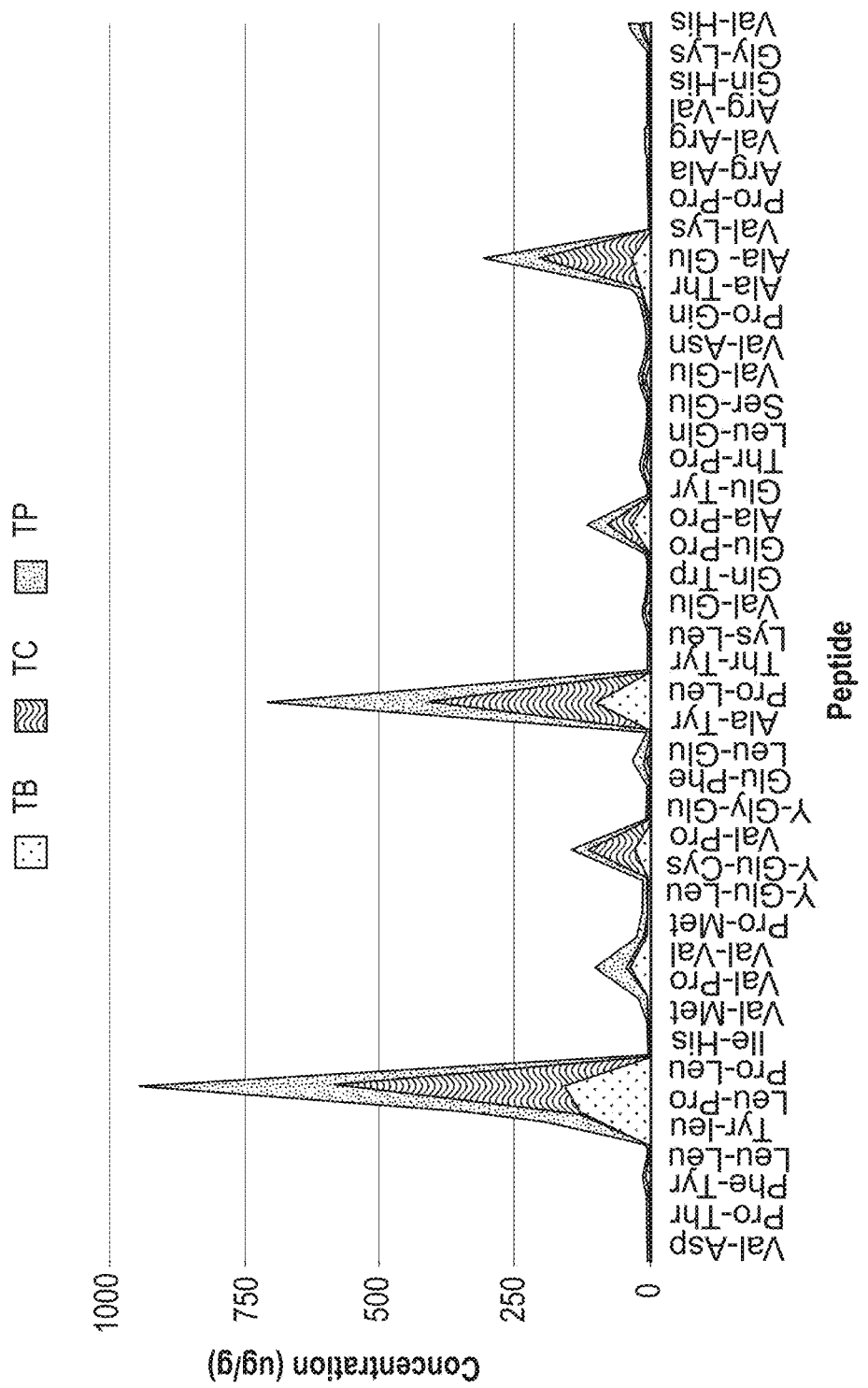
FIG. 6B is a graph illustrating alternative embodiments of compositional profiles of reference products in accordance with the disclosed subject matter.
Figure 6C:
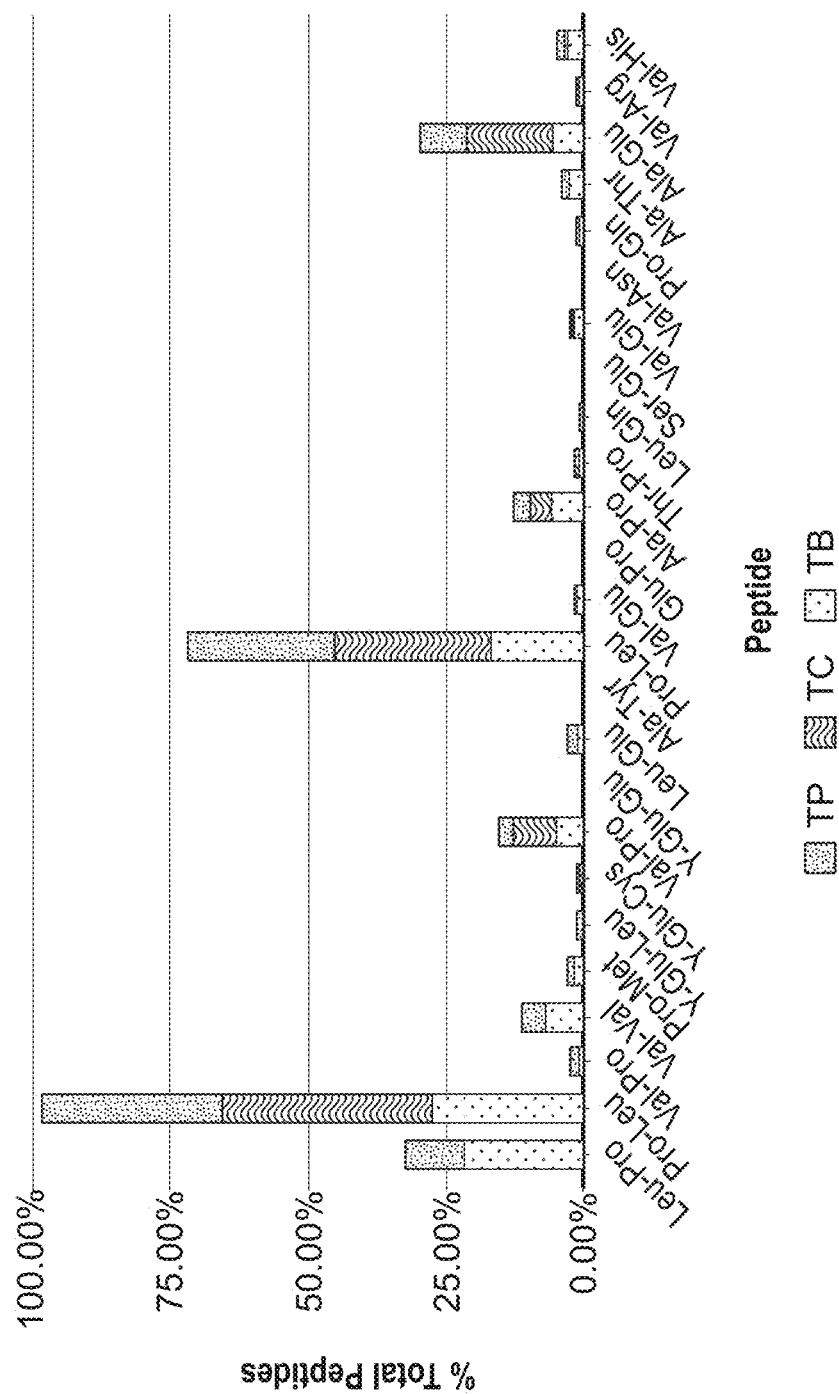
FIG. 6C is a graph illustrating selected portions of the graph of FIG. 6B on a normalized scale for purpose of illustration and comparison.
Figure 6D:
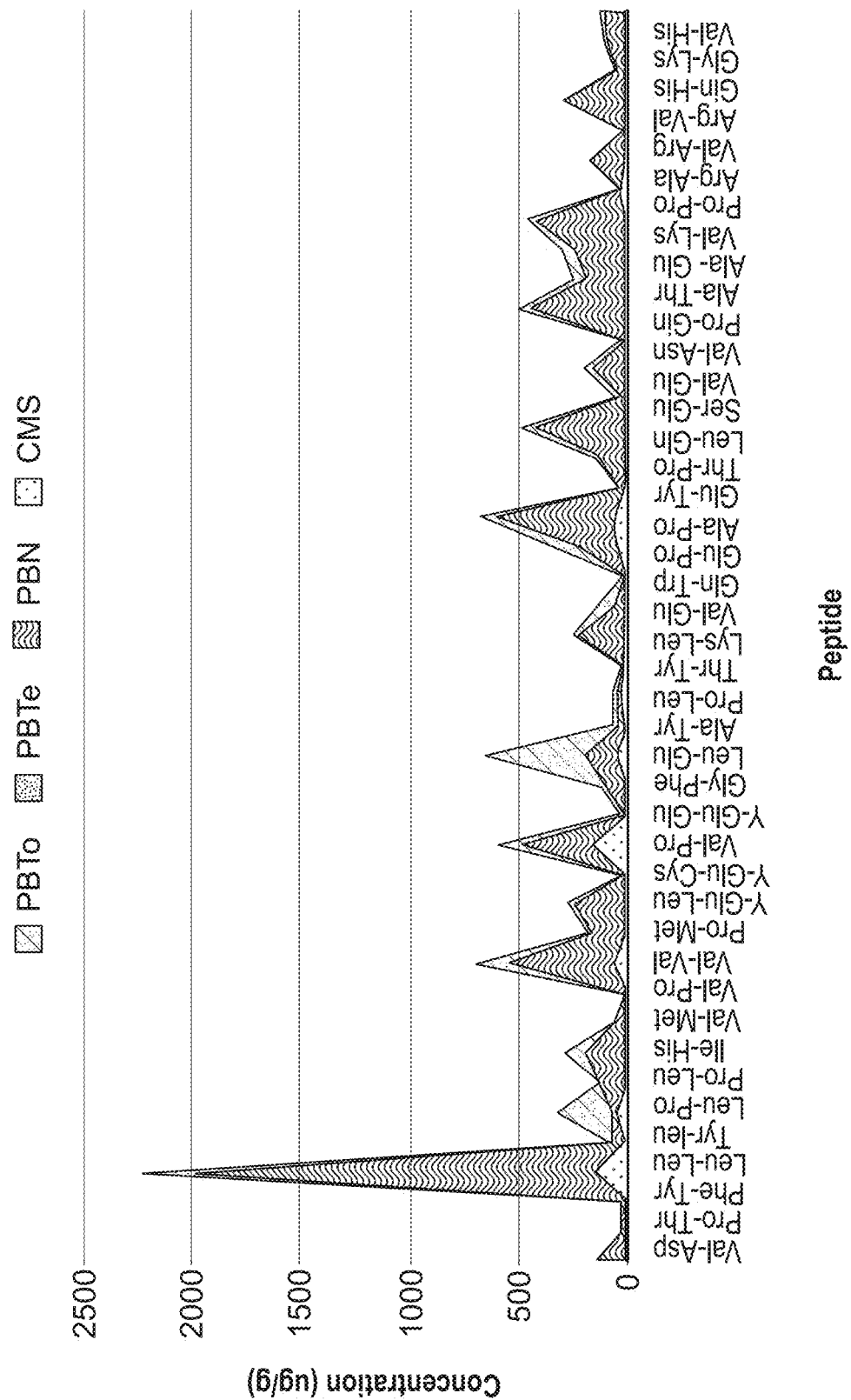
FIG. 6D is a graph illustrating alternative embodiments of compositional profiles of base cellular agriculture products, shown for purpose of illustration and comparison with the compositional profiles of FIGS. 6B and 6C.

Additionally, with reference to FIGS. 6B and 6C, for example and not limitation, dipeptides present in traditional meat products are shown, including traditional pork (TP), traditional chicken (TC), and traditional beef (TB). Moreover, with reference to FIG. 6D, for purpose of illustration and comparison, dipeptides present in cultivated meat and meat substitute products, including plant-based tofu (PBTo), plant-based tempeh (PBTe), plant-based natto (PBN) and cultivated meat substitutes (CMS), are shown. Dipeptides and free amino acids can be considered as flavor precursors in various food products. Moreover, as shown, compositions of free amino acids, peptides, and nucleotides in meat substitutes can differ significantly from compositions of traditional meat and traditional plant-based foods.

As embodied herein, extraction-quantification component 106 can perform extraction of kokumi or umami peptides from the sample of cultivated meat tissue, for example using a homogenizer. For example and without limitation, the kokumi or umami peptides can be extracted using an extraction solution with a solvent, which can include ethanol, methanol, acetonitrile, formic acid, acetic acid, triethanolamine, or trichloroacetic acid in water. Additionally or alternatively, as embodied herein, the sample can be frozen in liquid nitrogen before homogenizing the sample of cultivated meat tissue in an extraction solution with a cell homogenizer to obtain an analytical sample. The analytical sample can be diluted in a dilution solution as described herein.

Furthermore, or as an alternative, as embodied herein, the analytical sample can be subjected to chromatographic separation and detected with a detector as described herein. The concentration of at least one nucleotide and/or at least one kokumi or umami peptide in the sample of cultivated meat can be determined from the output of the detector.

As embodied herein, both the extraction solution and the dilution solution can include a first reference standard with a known response ratio relative to the at least one peptide in the detector, and a second reference standard with a known response ratio relative to the at least one peptide in the detector. Additionally, the dilution solution can further include a third standard with a known response ratio in the detector.

Figure 7A:
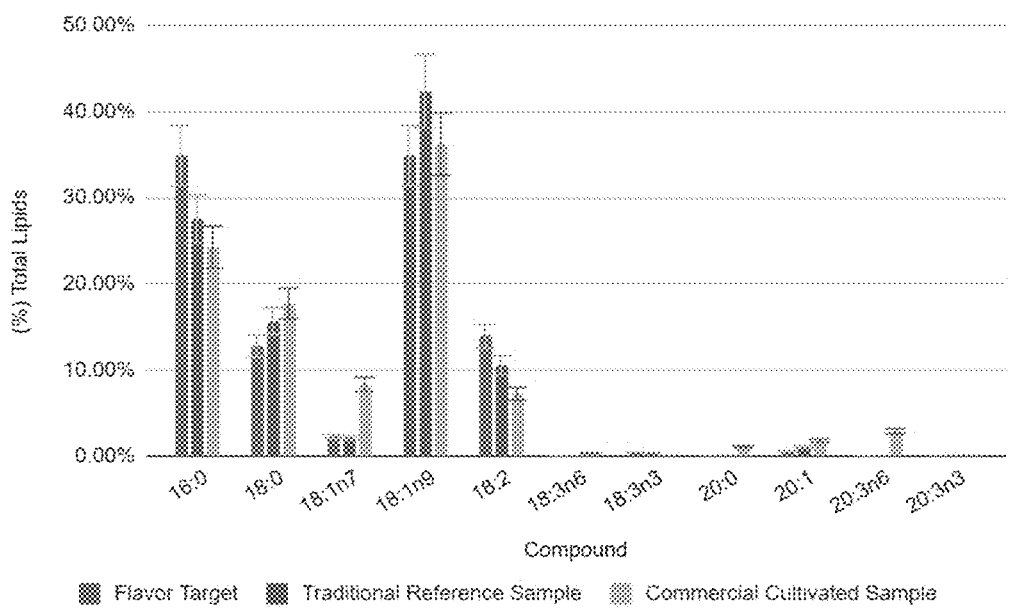
FIG. 7A is a graph illustrating exemplary embodiments of compositional profiles of a reference product, a base cellular agriculture product and a target product shown side-by-side for purpose of illustration and comparison.

With reference to FIG. 7A, a lipid profile of a traditional commercial product and a commercial cultivated animal product are shown. As shown in FIG. 7A, for purpose of illustration and not limitation, gap analysis of the flavor compounds identifies deficiencies and areas for flavor improvement in the commercial cultivated animal product, for example in the compounds denoted by an asterisk in the figure. The denoted fatty acids can be identified as contributing significantly to organoleptic qualities, such as meaty flavors and precursors to volatiles, which can give rise, for example to distinctive odors of meat. Components lacking such components can lead to a consumer considering a product to taste bland or lacking in robustness, due at least in part to perception of umami and kokumi (e.g., continuity, mouthfullness, richness and thickness) attributes.

Figure 7B:
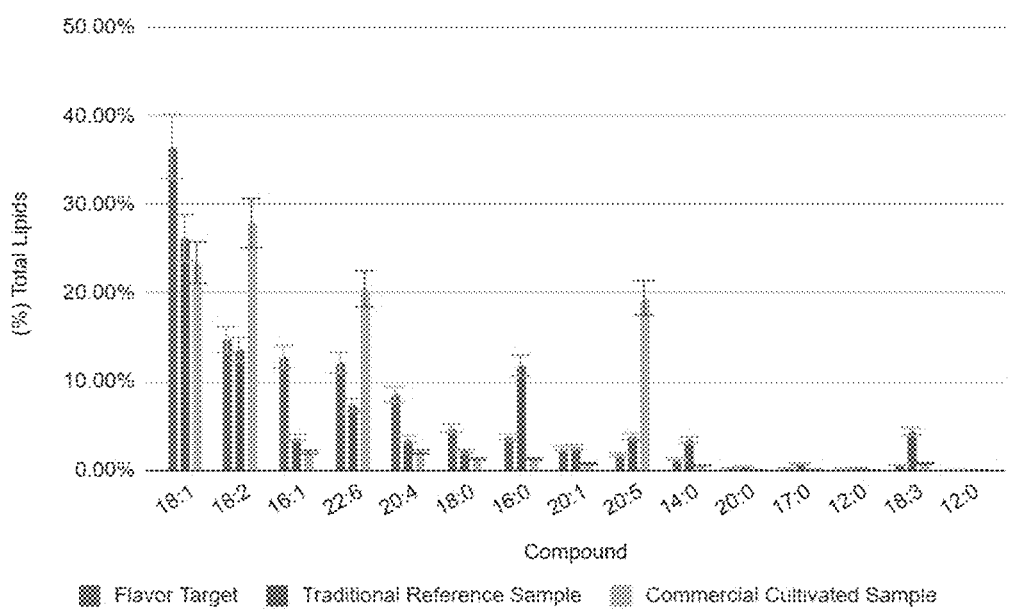
FIG. 7B is a graph illustrating alternative embodiments of compositional profiles of a reference product, a base cellular agriculture product and a target product shown side-by-side for purpose of illustration and comparison.

With reference to FIG. 7B, a lipid profile of a traditional commercial product and a commercial cultivated seafood product are shown. As shown in FIG. 7B, for purpose of illustration and not limitation, gap analysis of the flavor compounds identifies deficiencies or overabundance, as well as areas for flavor improvement in the commercial cultivated seafood product, for example in the compounds denoted by an asterisk in the figure. As shown, several compounds were found to be in a large excess, which can react with oxygen to produce primary oxidation products, which can be highly unstable. Overabundance of these compounds can break down rapidly and produce a wide variety of secondary components, which can be responsible for the formation of rancid, fishy and/or metallic off-flavors.

Figure 8A:
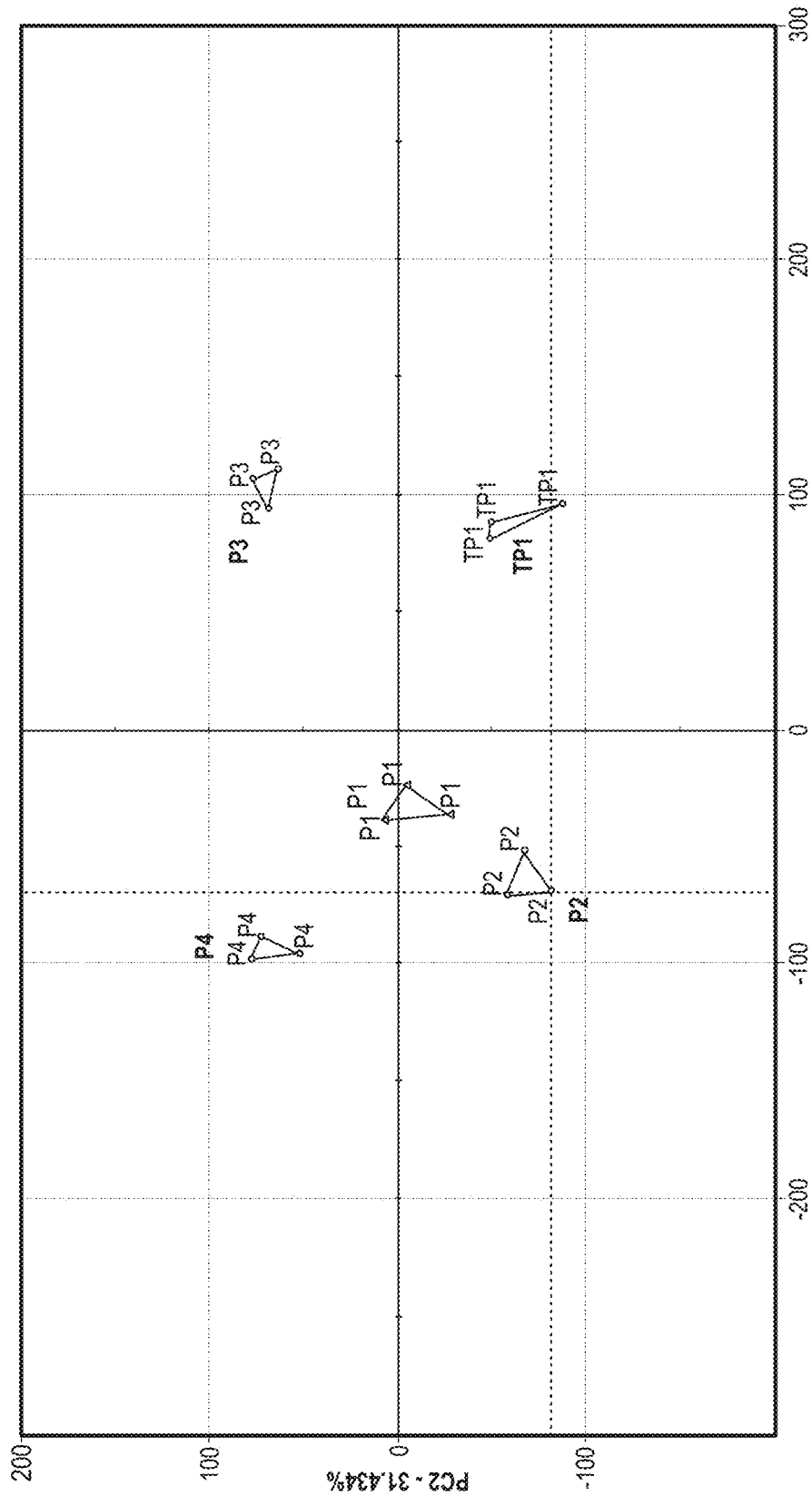
FIG. 8A is a graph illustrating alternative embodiments of compositional profiles of a reference product and base cellular agriculture products in accordance with the disclosed subject matter.
Figure 8B:
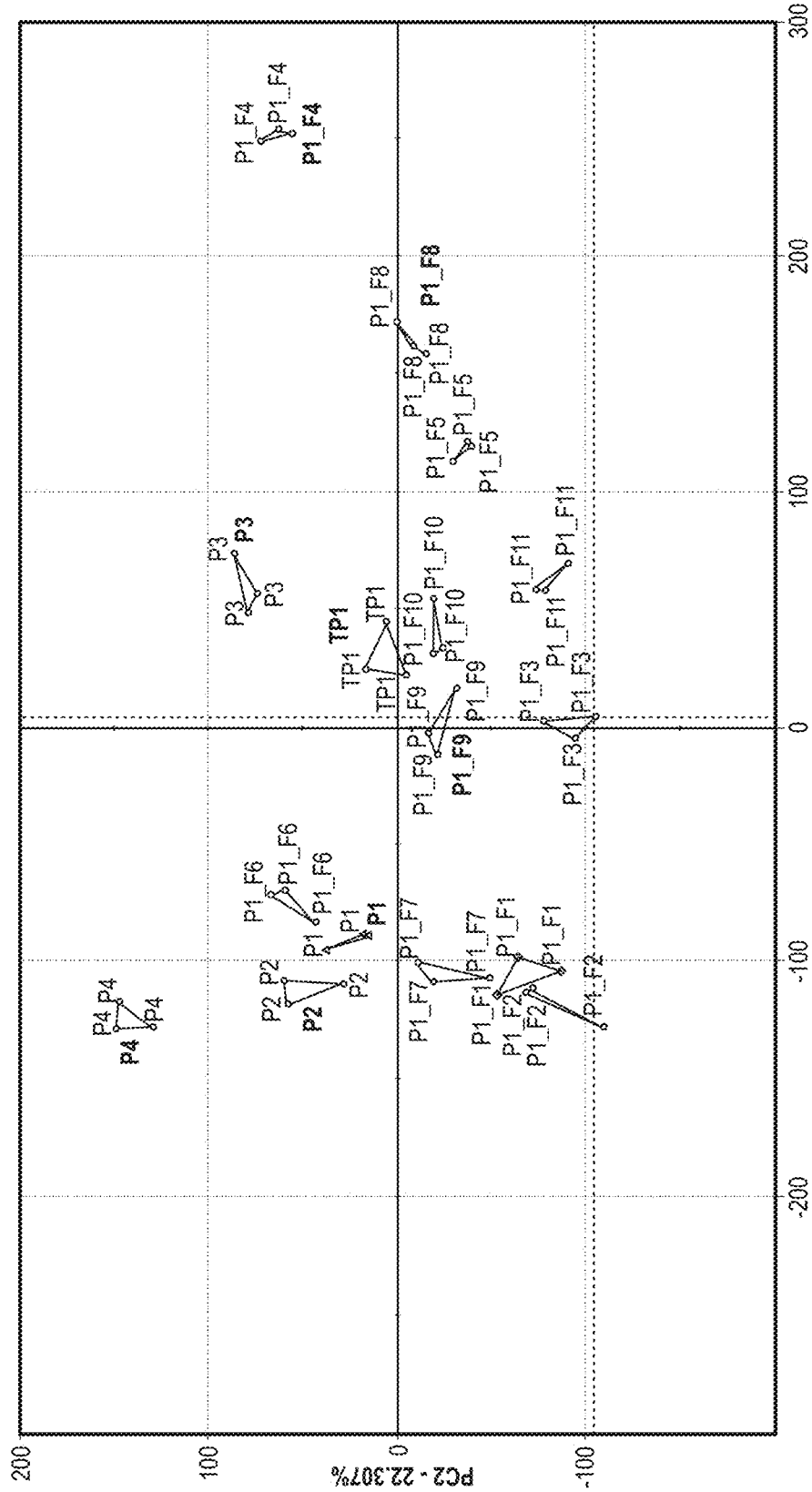
FIG. 8B is a graph illustrating alternative embodiments of compositional profiles of a reference product, base cellular agriculture products, and enhanced cellular agriculture products in accordance with the disclosed subject matter.

By way of another example, for purpose of illustration only and not limitation, other attributes affecting flavor can be analyzed using the systems and methods of the disclosed subject matter. With reference to FIGS. 8A-8B, compositional profiles of a reference product, base cellular agriculture products and enhanced cellular agriculture products are shown. In this example, extraction-quantification component 106 can include an electronic nose and/or an electronic tongue to analyze the molecular composition of samples of the various products.

Referring still to FIGS. 8A-8B, for purpose of illustration and not limitation, as embodied herein, the reference product can include a commercial organic low-fat cow milk product (TP1). As shown in FIG. 8A, as embodied herein, base cellular agriculture products and other reference products analyzed for flavor component identification and alignment with the reference product can include a commercial cultivated milk product (P1), a commercial animal-free dairy milk product (P2), a commercial whole cow milk product (P3) and a commercial plant-based milk product (P4). Referring now to FIG. 8B, enhanced cellular agriculture products including P1 combined with 11 different formulations (P1+F1–P1+F11) of culture supplement compositions 1000 prepared as described herein. Additional details of the formulations are shown, for example only and without limitation, and as embodied herein, in Table 1 below.

With continued reference to FIGS. 8A-8B, the products were analyzed using an electronic tongue (e.g., Astree e-tongue system, AST-5052 by Alpha MOS) to compare compositional profiles of products P1–P4 compared to the reference product TP1. As shown in FIGS. 8A-8B, a flavor map of TP1 compared to products P1-P4 as well as formulations P1+F1 through P1+F11 can be produced using principal component analysis (PCA) of selected sensors of the electronic tongue. Based on the comparison, for example as shown from the proximity of products P1-P4 to TP1, the flavor profile of TP1 can be considered slightly closer to P3 than P1, P2 and P4. Additionally, for example as shown from the proximity of formulations P1+F1 through P1+F11 to TP1, the flavor profile of formulations P1+F9, P1+F10 and P1+F3 can be considered closest to TP1. Thus, the flavor profile of formulations P1+F9, P1+F10 and P1+F3 can be considered substantially aligned with the reference product TP1.

to be added to the cellular agriculture product in later phases, such as during the structuring phase.

Figure 10A:
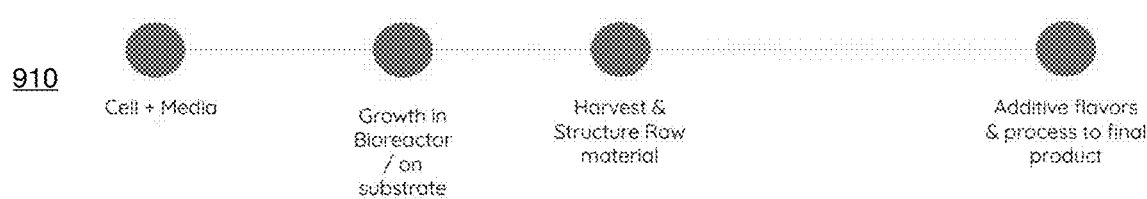
FIGS. 10A-10C each is a diagram illustrating an alternative embodiment of a manufacturing process for a cellular agriculture product in accordance with the disclosed subject matter.

Referring now to FIG. 10A, for purpose of illustration only and not limitation, an exemplary manufacturing process for a cultivated food product is shown. As shown in FIG. 10A, for example and without limitation, manufacturing process 910 for a cultivated food product can include cell and media creation, growth (e.g., in a bioreactor or on a substrate), harvest and structure raw material, and additive flavoring and processing into a final product. As embodied herein, system 100 and method 200 can adjust the manufacturing process during the cell and media creation phase and/or the growth phase of the cultivated food product manufacturing process as described herein to affect attributes of interest, including but not limited to flavor. Such adjustment during these earlier phases can reduce or eliminate the use of additives, including but not limited to flavoring additives, to be added to the cultivated food product in later phases, such as during the additive flavoring and processing phase.

Figure 10B:

Referring now to FIG. 10B, for purpose of illustration only and not limitation, an exemplary manufacturing process for a precision fermented product is shown. As shown in FIG. 10B, for purpose of illustration and not limitation, manufacturing process 920 for a precision fermented prod-

TABLE 1

| Name | Label | Formulation Description | Sample Preparation |
|---|---|---|---|
| Formulation 1 | P1 + F1 | 1% w/v Glycoside hydrolase | 25 mL of Product 1 + 2.5 mL 10% w/v solution |
| Formulation 2 | P1 + F2 | 1% w/v Transferase | 25 mL of Product 1 + 2.5 mL 10% w/v solution |
| Formulation 3 | P1 + F3 | 1% v/v Endopeptidase | 25 mL of Product 1 + 2.5 mL liquid sample |
| Formulation 4 | P1 + F4 | 1% v/v Exopeptidase | 25 mL of Product 1 + 2.5 mL liquid sample |
| Formulation 5 | P1 + F5 | 1% v/v Triacylglycerol acyl hydrolase | 25 mL of Product 1 + 2.5 mL 10% w/v solution |
| Formulation 6 | P1 + F6 | 0.3% w/v Peroxidase | 25 mL of Product 1 + 2.5 mL 5% w/v solution |
| Formulation 7 | P1 + F7 | 1% w/v 1:1 Hydrolase/Transferase blend | 25 mL of Product 1 + 2.5 mL 10% w/v solution |
| Formulation 8 | P1 + F8 | 1% v/v 1:1 Hydrolase, peroxidase | 25 mL of Product 1 + 2.5 mL liquid sample |
| Formulation 9 | P1 + F9 | 1% w/v Desaturase + 1% v/v Fish oil Blend: 180 mg EPA, 120 mg DHA, 5 mg cholesterol, | 25 mL of Product 1 + 2.5 mL liquid sample |
| Formulation 10 | P1 + F10 | 1% w/v Desaturase + 1% v/v Fish oil Blend: 180 mg EPA, 120 mg DHA, 5 mg cholesterol, +500 mg Linoleic and 500 mg Oleic acid | 25 mL of Product 1 + 2.5 mL liquid sample |
| Formulation 11 | P1 + F11 | 1% w/v Desaturase + 1% w/w Amino Acid blend: Serine 0.5 mg, 0.1 mg Methionine, 0.1 mg Glycine, 0.1 mg Glutamic Acid, 0.1 mg Arginine, 0.1 mg Tyrosine, 0.1 mg Aspartic Acid, 0.1 mg Leucine | 25 mL of Product 1 + 2.5 mL 10% w/v solution |

Figure 9:
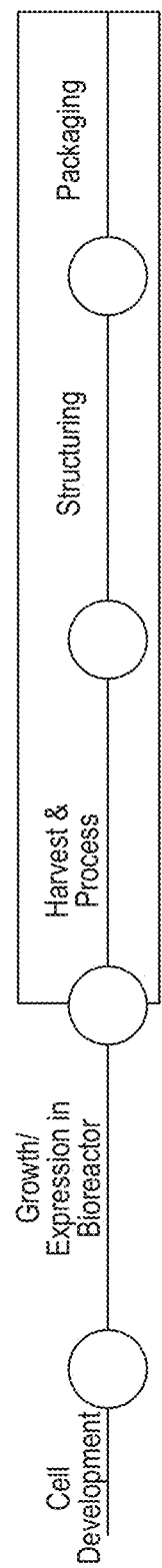
FIG. 9 is a diagram illustrating an exemplary embodiment of a manufacturing process for a cellular agriculture product in accordance with the disclosed subject matter.

Referring now to FIG. 9, an exemplary manufacturing process for a cellular agriculture product is shown. As shown in FIG. 9, for purpose of illustration and not limitation, manufacturing process 900 for a cellular agriculture product can include cell development, growth/expression (e.g., in a bioreactor), harvest and processing, structuring, and packaging. As embodied herein, system 100 and method 200 can adjust the manufacturing process during the growth/expression phase of the cellular agriculture product manufacturing process as described herein to affect attributes of interest, including but not limited to flavor. Such adjustment during the growth/expression phase can reduce or eliminate the use of additives, including but not limited to flavoring additives, uct can include feedstock and microorganism creation, growth and expression (e.g., in a bioreactor), harvest protein (e.g., involving killing the microorganism and/or purification of target protein), drying or lyophilization of target protein, rehydration of target protein, combining with other ingredients for base solution, additive flavoring and processing into a final product. As embodied herein, system 100 and method 200 can adjust the manufacturing process during the growth and expression phase, during the rehydration phase, or in a base solution of a precision fermented product manufacturing process as described herein to affect attributes of interest, including but not limited to flavor. Such adjustment during these growth and expression, rehydration phase, or base solution can reduce or eliminate the use of additives, including but not limited to flavoring additives, to be added to the precision fermented product in later phases, such as during the additive flavoring and processing phase.

Figure 10C:

Referring now to FIG. 10C, for purpose of illustration only and not limitation, an exemplary manufacturing process for a plant-based substitute product is shown. As shown in FIG. 10C, for example and without limitation, manufacturing process 930 for a plant-based substitute product can include growing, planting and harvesting, processing ingredients, extruding, encapsulation or restructuring, and additive flavoring and processing into a final product. As embodied herein, system 100 and method 200 can adjust the manufacturing process during the growth phase and/or processing ingredients phase of the plant-based substitute product manufacturing process as described herein to affect attributes of interest, including but not limited to flavor. Such adjustment during these earlier phases can reduce or eliminate the use of additives, including but not limited to flavoring additives, to be added to the plant-based substitute product in later phases, such as during the additive flavoring and processing phase.

According to other aspects of the disclosed subject matter, culture supplement compositions for producing an enhanced cellular agriculture product are provided. In accordance with the disclosed subject matter herein, a culture supplement composition for producing an enhanced cellular agriculture product, includes a formulation including at least one enzyme in a carrier. As embodied herein, the formulation can be configured to adjust production of a base cellular agriculture product to produce an enhanced cellular agriculture product without reducing or inhibiting biomass production or cellular viability compared to the base cellular agriculture product. Additionally or alternatively, as embodied herein, the culture supplement composition can further include, in the carrier, at least one of a substrate or an additive.

Figure 11:
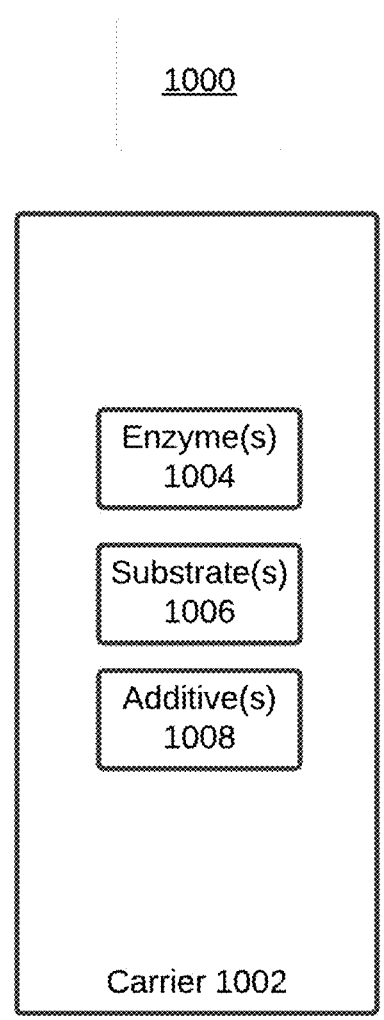
FIG. 11 is a diagram illustrating an exemplary embodiment of a culture supplement composition for a cellular agriculture product in accordance with the disclosed subject matter.

For purpose of illustration and not limitation, reference is made to the exemplary embodiments of culture supplement compositions shown in FIGS. 11-13B. With reference to FIG. 11, a culture supplement composition 1000 can generally include, in a carrier 1002, one or more enzyme(s) 1004. Culture supplement composition 1000 can further include, as embodied herein, one or more substrate(s) 1006 or additive(s) 1008 in carrier 1002. As embodied herein, culture supplement composition 1000 can be configured to adjust production of a base cellular agriculture product to produce an enhanced cellular agriculture product without reducing or inhibiting biomass production or cellular viability compared to the base cellular agriculture product.

As embodied herein, carrier 1002 can include an emulsifier solution, powder, gel, or solid substrate. For example and without limitation, the emulsifier solution can include one or more of a nonionic detergent, a nonionic triblock copolymer, a nonionic surfactant, a poloxamer, and a zwitterionic detergent. As embodied herein, carrier 1002 can have a concentration from 0.5% v/v to 5% v/v.

Additionally or alternatively, as embodied herein, enzyme(s) 1004 can include one or more of a fatty acid desaturase, a cyclooxygenase, a lipoxygenase, an elongase, an oxidoreductase, a transferase, an endopeptidase, an exopeptidase, a hydrolase, a lyase, an isomerase, or a ligase. For example and without limitation, enzyme(s) 1004 can have a concentration from 0.1% w/v to 3% w/v with enzymatic activity from 20000 to 20 units/mg.

Furthermore, or as an alternative, as embodied herein, substrate(s) 1006 can include one or more of a saturated fatty acid, a monounsaturated fatty acid, a polyunsaturated fatty acid, an omega-3 fatty acid, an omega-6 fatty acid, a peptide, a protein, a nucleotide or an amino acid. For example and without limitation, substrate(s) 1006 can have a concentration from 0.1 mM to 50 mM. Additionally or alternatively, substrate(s) 1006 can have a concentration from 0.1 mg/mL to 1 mg/mL.

In addition, or as a further alternative, as embodied herein, additive(s) 1008 can include one or more of a growth factor protein, an insulin hormone, and a transport protein.

Culture supplement composition 1000 can be made, for example and without limitation, by mixing the components of the culture supplement composition 1000 in the amounts or proportions described herein. Moreover, or as an alternative, each component of the culture supplement composition 1000 can be added to a vessel in a sterile environment (e.g., a flask or beaker) in specified amounts and mixed until homogeneity. Additionally or alternatively, as embodied herein, processing circuitry 104 can control, directly or indirectly, operation of a mixer to produce culture supplement compositions 1000 as described herein.

Culture supplements can include, for purpose of illustration and not limitation, media supplements for cultivated agriculture products, supplements for precision fermentation, and other supplements for production of cellular agriculture products. Culture supplement composition 1000 can be formulated to be added to a cell culture medium used to produce cells of a base cellular agriculture product at a concentration from 1% v/v to 15% v/v. For purpose of illustration and not limitation, culture supplement composition can be configured to modify at least one of a growth phase, an expression phase, a rehydration phase, an encapsulation or a restructuring phase of the base cellular agriculture product. As embodied herein, culture supplement composition 1000 can be configured to modify a growth phase or an expression phase of the base cellular agriculture product, which can be prior to a structuring, restructuring, or other phase involving use of additives to improve attributes of the base cellular agriculture product. Culture supplement composition 1000 can be added to a growth media in a production vessel, such as a bioreactor or other vessel suitable for biomass growth. Additionally or alternatively, as embodied herein, processing circuitry 104 can be configured to control, directly or indirectly, operation of manufacturing component 108 including the production vessel. Culture supplement composition 1000 can thus be used to grow cells to produce an enhanced cellular agriculture product made using culture supplement composition 1000 as described herein. As embodied herein, the enhanced cellular agriculture product can have a similar cellular growth or cellular viability compared to the base cellular agriculture product.

Using cellular agriculture food products by way of example only and not limitation, attributes affecting flavor can be enhanced using the systems, compositions and techniques of the disclosed subject matter. As embodied herein, an enhanced cellular agriculture product can be produced, for example and without limitation, by enriching the cultivated cell biomass high value lipids by subjecting the cells in growth medium supplemented with a culture supplement composition 1000 embodied herein as a media supplement composition for cultivated cell production. In this manner, cellular flavoring of cellular agriculture products can be performed, which can enhance the compositional profiles of cultivated foods to target compounds involved in flavor development through bioengineered culture supplements that mimic environmental factors, and influence cells to create their own flavor profiles. Additionally or alternatively, as embodied herein, machine learning can be used to map the connections between media formulation, compositional profile and flavor alignment, which can suggest adjustments to one or more manufacturing processes or manufacturing components 108 used to make cultured media to achieve a desired flavor profile.

For purpose of illustration and not limitation, as embodied herein, culture supplement composition 1000 can provide for the simultaneous, substantially simultaneous or concurrent enhancement of lipids important for flavor in cultured cells, such as myocytes, adipocytes, chondrocytes, and fibroblasts used for food products using a formulated mixture in appropriate proportion to supplement the cell culture medium in a single reaction vessel.

As embodied herein, various techniques can be used for the cultivation of animal cells in vitro, including the use of scaffolds, bioreactors, and microcarriers to promote cell growth and differentiation. Moreover, as embodied herein, cell growth media conditions can be adjusted to enhance lipid compositional profiles in cultured cells. As such, as embodied herein, lipid accumulation and concomitant biomass production from cultivated cells can be enhanced during cell growth and fermentation. Using culture supplement composition 1000, the development of flavor compounds can be based at least in part on the cell's own machinery to provide biochemical synthesis of specific compounds. In this manner, the supplementation of enzymes and substrates in a growth medium can improve lipid content with simultaneous high biomass productivities.

In this example, fatty acid and biomass production rates of different species were compared in nutrient rich/deficient fermentation conditions by supplementing chemical substrate in unique combinations in nutrient rich conditions only. This example resulted in increased biomass and lipid production, due at least in part to the cumulative synergistic effect of the ratio of substrates and enzymes used, compared to conventional techniques.

As embodied herein, culture supplement composition 1000 can be added to enhance lipid and biomass in tandem during cell growth in a bioreactor. Culture supplement composition 1000 can thus supplement specific amounts of enzymes, substrates, additives and emulsifiers in a formulated solution, whereby the production of lipids in the biomass is enhanced concomitantly. In this manner, negative effects on biomass and high value lipids can be overcome.

Additionally or alternatively, as embodied herein, culture supplement composition 1000 can be used for enhancing lipid constituents in cultured cells such as myocytes, adipocytes, chondrocytes, and fibroblasts without compromising the biomass production and cell viability. In this example, culture supplement composition 1000 can include at least one enzyme (e.g., a fatty acid desaturase, cyclooxygenase, lipoxygenase, elongase, oxidoreductase, transferase, endopeptidase, exopeptidase, hydrolase, lyase, isomerase, or ligase), at least one substrate (e.g., linoleic acid (LA), α-linolenic acid, di-homo-γ-linoleic acid, oleic acid, arachidonic acid, heptadecenoic acid, stearic acid, and palmitoleic acid, a peptide, a protein, a nucleotide or an amino acid), at least one additive (e.g., insulin, transferrin, FGF1, FGF2, IGF2, TGF-β1, GDF-8, VEGF, LIF) and an emulsifier solution (e.g., Triton X-100, Pluronic F-68, Tween 20, Tween 80, Nonidet P-40 and CHAPS).

Figure 12A:
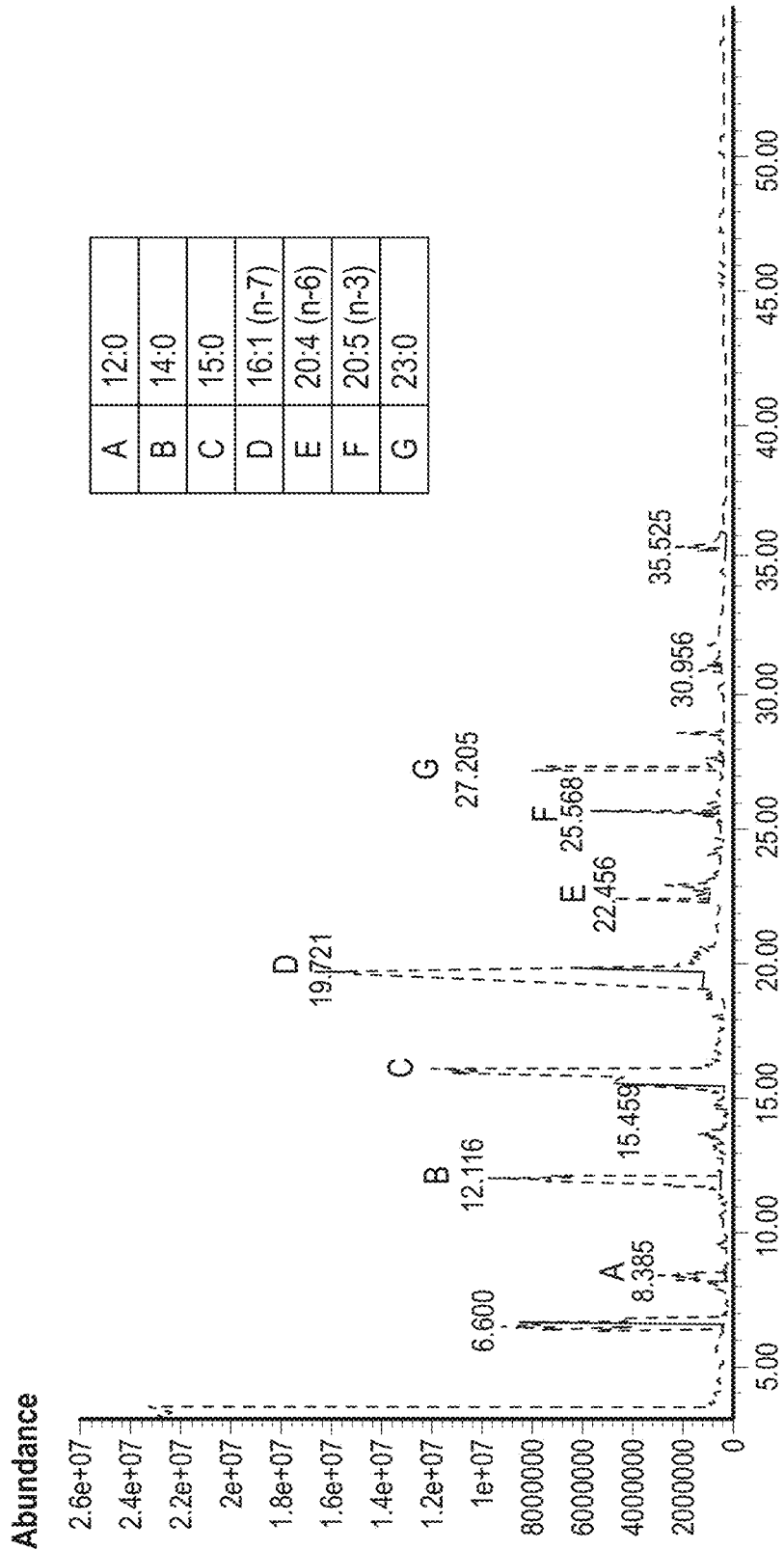
FIG. 12A is a graph illustrating an exemplary embodiment of a compositional profile of a reference product in accordance with the disclosed subject matter.
Figure 12B:
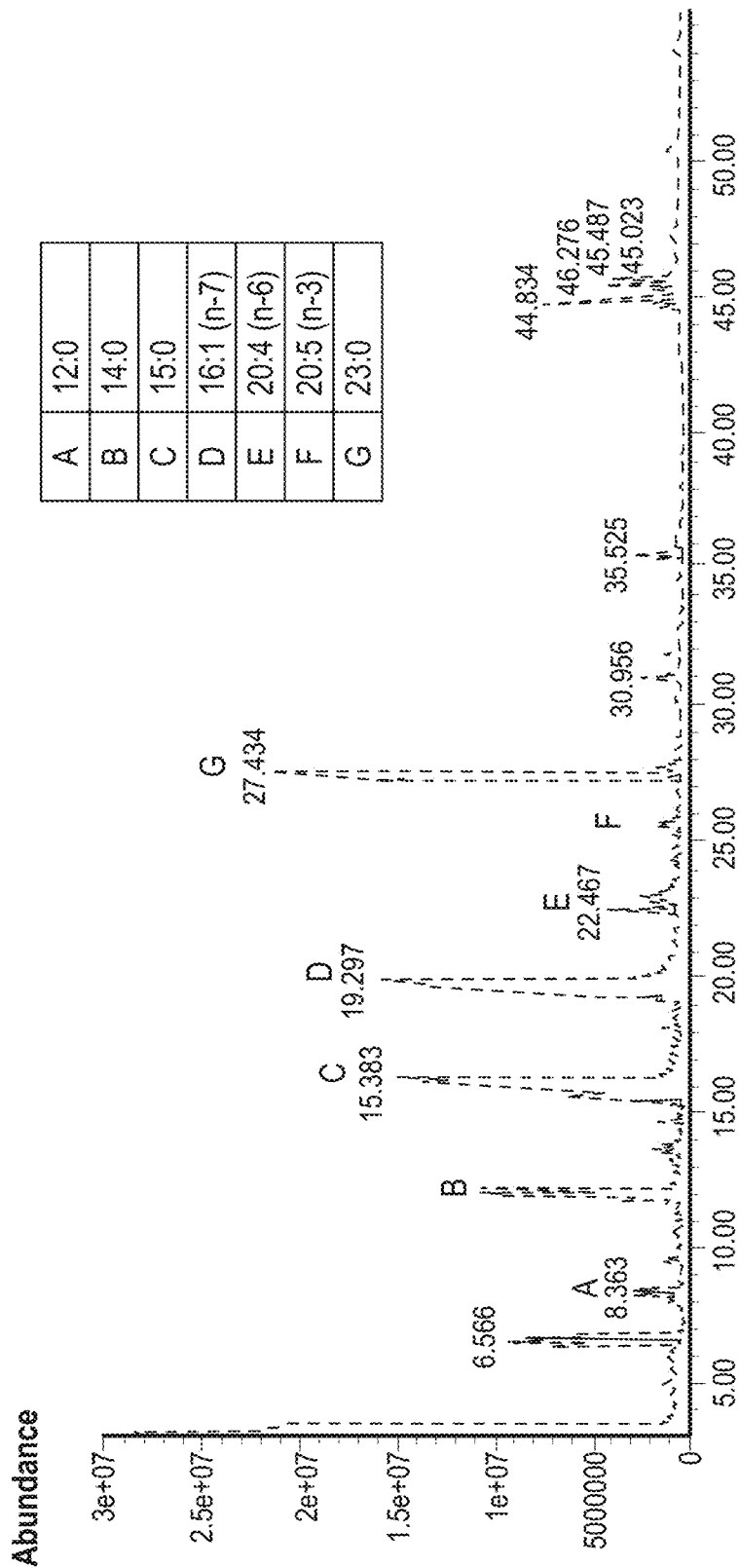
FIG. 12B is a graph illustrating an exemplary embodiment of a compositional profile of a cellular agriculture product produced using a culture supplement composition in accordance with the disclosed subject matter, shown side-by-side with the compositional profile of FIG. 12A for purpose of illustration and comparison.

Referring now to FIGS. 12A-12B, lipid profiles of traditional salmon cells, extracted using extraction-quantification component 106 and analyzed without using culture supplement composition 1000, are shown in FIG. 12A for comparison with lipid profiles of traditional salmon cells, extracted using extraction-quantification component 106 and analyzed after exposure to culture supplement composition 1000, shown in FIG. 12B. As shown in FIGS. 12A-12B, the fatty acid (FA) profile of traditional salmon cells exposed to culture supplement composition 1000 additionally showed extra peaks, which can correspond to an increase in longer chain fatty acids. Moreover, based at least in part on retention times, the additional peak (G) was identified as 23:0 using NIST 14 Database and quantitative analysis software (e.g., MassHunter software by Agilent).

As embodied herein, the accumulation of lipids in cultured cells can be provided through the use of culture supplement composition 1000 and extraction-quantification 106 for analysis of cultured myocytes, adipocytes, chondrocytes, and/or fibroblasts cells.

Additionally or alternatively, as embodied herein, cells can be cultured using culture supplement composition 1000 to supplement cell culture media. Supplementation with culture supplement composition 1000 can allow a culturing process including continuous growth and/or fermentation for enhancing lipid accumulation and biomass in tandem in a single reaction vessel.

Furthermore, or as an alternative, as embodied herein, the amount of culture supplement composition 1000 to be added to a cell culture can vary depending on various factors, including but not limited to growth conditions and the type of cells to be grown. For example and as embodied herein, culture supplement composition 1000 can be added to the cell culture media at concentrations from 1% v/v to 15% v/v.

As embodied herein, cells cultured as described herein can be used for cultivated or lab-grown food products. Methods for formulating culture supplements to improve lipid profiles in cultivated cells and for assessing and/or verifying such profiles are thus provided in this example.

Additionally or alternatively, as embodied herein, culture supplement composition 1000 can include at least one enzyme selected from enzymes with activity of a fatty acid desaturase, a cyclooxygenase, a lipoxygenase, an elongase, an oxidoreductase, a transferase, an endopeptidase, an exopeptidase, a hydrolase, a lyase, an isomerase, or a ligase; at least one substrate selected from linoleic acid (LA), α-linolenic acid, di-homo-γ-linoleic acid, oleic acid, arachidonic acid, heptadecenoic acid, stearic acid, palmitoleic acid, a peptide, a protein, a nucleotide or an amino acid; at least one additive selected from epidermal growth factors, keratinocyte growth factors, insulin-like growth factors (IGF2), fibroblast growth factors (FGF1/2), transforming growth factor (TGF-β1/2), insulin, transferrin, GDF-8, and/or VEGF; and an emulsifier solution selected from Triton X-100, Pluronic F-68, Tween 80, Nonidet P-40 and/or CHAPS.

The disclosed subject matter also provides methods for formulating culture supplements which can enhance the flavor constituents of cultured cells for food product applications, as embodied herein using a small amount of sample, e.g., less than 2 grams, for analysis.

As embodied herein, a culture supplement composition for enhancing the production of subsets of free fatty acid compounds in food that impact flavor in cultured cells, such as myocytes, adipocytes, chondrocytes, and fibroblasts, without compromising the biomass production and cell viability can be provided using culture supplement composition 1000. Moreover, as embodied herein, culture supplement composition 1000 can include at least one enzyme selected from enzymes having activity of a fatty acid desaturase, a cyclooxygenase, a lipoxygenase, an elongase, an oxidoreductase, a transferase, an endopeptidase, an exopeptidase, a hydrolase, a lyase, an isomerase, or a ligase; at least one substrate selected from linoleic acid (LA), α-linolenic acid, di-homo-γ-linoleic acid, oleic acid, arachidonic acid, heptadecenoic acid, stearic acid, palmitoleic acid, a peptide, a protein, a nucleotide, or an amino acid; at least one additive selected from FGF1, FGF2, IGF2, insulin, transferrin, TGF-β1, GDF-8, and/or VEGF; and an emulsifier solution selected from Triton X-100, Pluronic F-68, Tween 80, Nonidet P-40 and/or CHAPS.

Additionally or alternatively, as embodied herein, the functional enzymes can be used at concentrations of 0.1% w/v to 3% w/v with enzymatic activity of 20000 to 20 units/mg; the substrates can be used at concentrations of 0.1 mM to 50 mM; the additives can be used at a concentration of 0.1 mg/mL to 1 mg/mL; and the emulsifier solution can be used at 0.5 to 5% v/v. The final concentration of culture supplement composition 1000 can be approximately 1% v/v to 15% v/v.

Furthermore, or as an alternative, enzymatic hydrolysis of the cultured fat, lipid or oil sample and extraction of the cultured fat sample can be performed in an extraction solution, thereby producing an analytical extract including the free fatty acids and free fatty acids dissolved in the extraction solution. As embodied herein, the extraction solution includes a solvent, such as ethanol, methanol, n-heptane, acetonitrile, formic acid, acetic acid, triethanolamine, or trichloroacetic acid in water; and an internal standard, which can be a saturated fatty acid such as myristic acid or lauric acid.

Figure 13A:
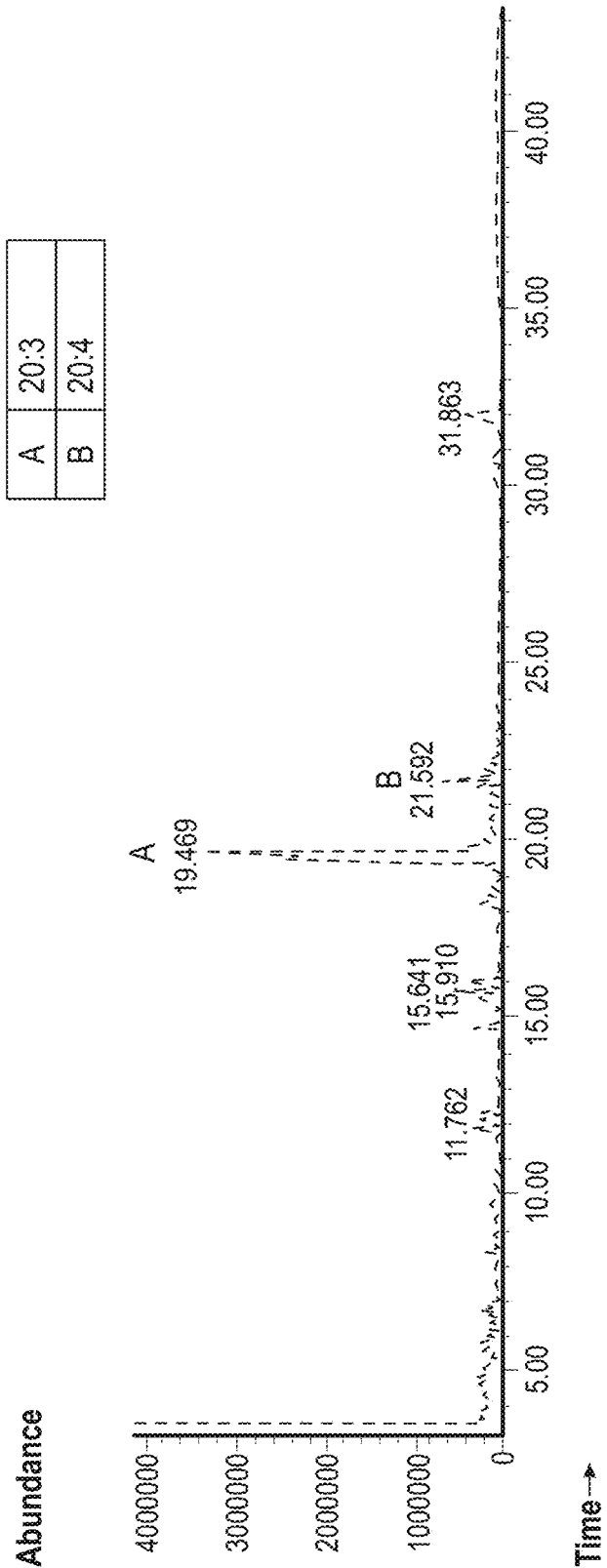
FIGS. 13A and 13B are graphs illustrating compositional profiles of an exemplary embodiment of a base cellular agriculture product (FIG. 13A) and a corresponding enhanced cellular agriculture product (FIG. 13B), for purpose of comparison and confirmation of the disclosed subject matter.
Figure 13B:
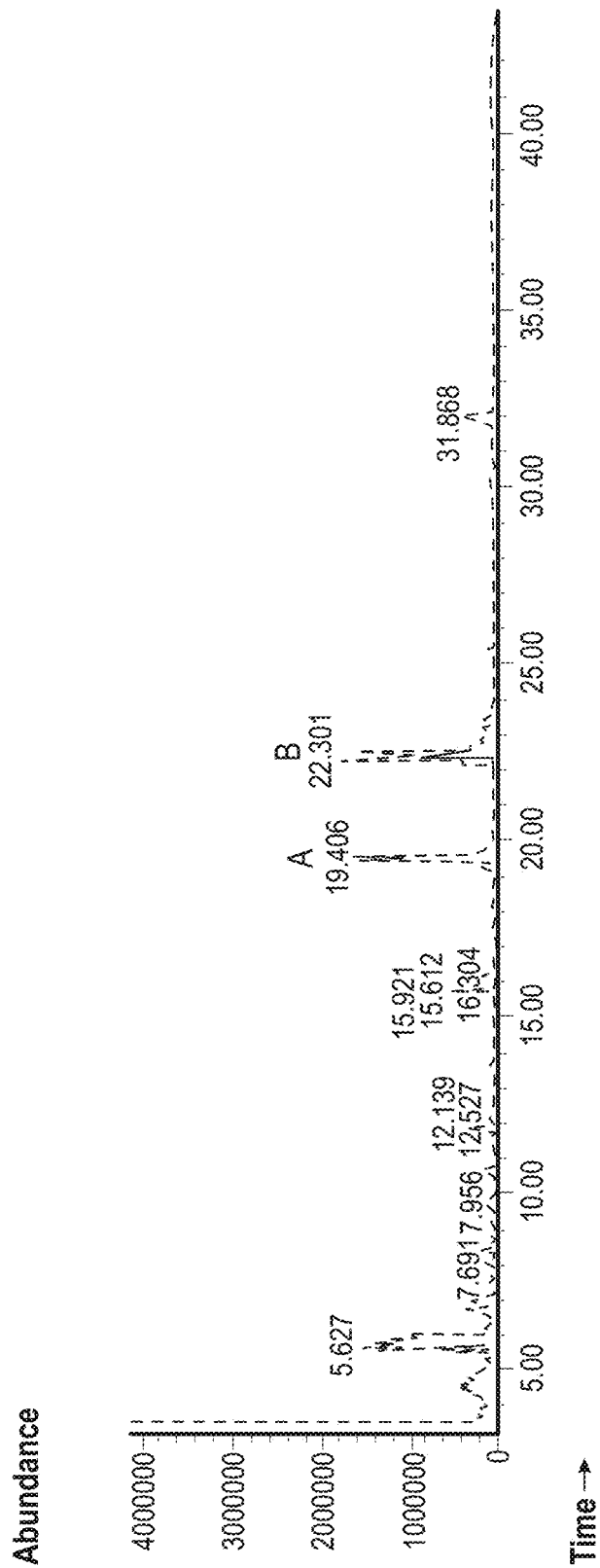

By way of another example, for purpose of illustration only and not limitation, FIGS. 13A and 13B illustrate exemplary results from use of an exemplary embodiment of culture supplement composition 1000. As embodied herein, culture supplement composition 1000 includes enzymes expressed in *E. coli*. As shown in FIGS. 13A and 13B, culture supplement composition 1000 can adjust the level of an identified component of interest of a base cellular agriculture product to produce the enhanced cellular agriculture product of FIG. 13B. For example and not limitation, as embodied herein, the identified component of interest is a longer chain fatty acid (e.g., 20:4) shown as peak B. Moreover, peak B was identified as 20:4, as embodied herein using NIST 14 Database and quantitative analysis software (e.g., MassHunter software by Agilent).

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A culture supplement composition for producing a cellular agriculture product, comprising:
   a formulation including, in a carrier, at least one enzyme comprising a desaturase, a substrate comprising eicosapentaenoic acid (EPA) and docosahexaenoic acid (DHA), and at least one additive comprising a cholesterol, wherein the formulation comprises 1% w/v of the desaturase, and
   wherein the formulation is configured to adjust production of a base cellular agriculture product comprising a food product by affecting a flavor of the base cellular agriculture product to produce an adjusted cellular agriculture product without reducing or inhibiting biomass production or cellular viability compared to the base cellular agriculture product.

2. The composition of claim 1, wherein the substrate has a combined concentration of EPA and DHA from 0.1 mg/mL to 1 mg/mL.

3. The composition of claim 1, wherein the carrier comprises an emulsifier solution, powder, gel or solid.

4. The composition of claim 3, wherein the emulsifier solution comprises one or more of a nonionic detergent, a nonionic triblock copolymer, a nonionic surfactant, a poloxamer, and a zwitterionic detergent.

5. The composition of claim 1, wherein the formulation is configured to be added to a cell medium of the base cellular agriculture product at a concentration from 1% v/v to 15% v/v.

6. The composition of claim 1, wherein the formulation is configured to modify a growth phase or an expression phase of the base cellular agriculture product in a bioreactor.

7. The composition of claim 1, wherein the base cellular agriculture product comprises a cultivated food.

8. The composition of claim 1, wherein the base cellular agriculture product comprises a precision fermented food.

9. The composition of claim 1, wherein the formulation comprises 1% v/v of a blend comprising the EPA, the DHA, and the cholesterol.

10. The composition of claim 9, wherein the blend comprises 180 milligrams of the EPA, 120 milligrams of the DHA, and 5 milligrams of the cholesterol.

11. A cell medium for producing a cellular agriculture product, the cell medium comprising a culture supplement composition comprising:
   a formulation including, in a carrier, at least one enzyme comprising a desaturase, a substrate comprising eicosapentaenoic acid (EPA) and docosahexaenoic acid (DHA), and at least one additive comprising a cholesterol, wherein the formulation comprises 1% w/v of the desaturase, and
   wherein the formulation is configured to adjust production of a base cellular agriculture product comprising a food product by affecting a flavor of the base cellular agriculture product to produce an adjusted cellular agriculture product without reducing or inhibiting biomass production or cellular viability compared to the base cellular agriculture product.

12. The medium of claim 11, wherein the carrier comprises an emulsifier solution, powder, gel or solid substrate.

13. The medium of claim 12, wherein the emulsifier solution comprises one or more of a nonionic detergent, a nonionic triblock copolymer, a nonionic surfactant, a poloxamer, and a zwitterionic detergent.

14. The medium of claim 11, wherein the formulation has a concentration from 1% v/v to 15% v/v in the cell medium.

15. The medium of claim 11, wherein the formulation is configured to modify a growth phase or an expression phase of the base cellular agriculture product in a bioreactor.

16. The medium of claim 11, wherein the base cellular agriculture product comprises a cultivated food.

17. The medium of claim 11, wherein the base cellular agriculture product comprises a precision fermented food.

18. The medium of claim 11, wherein the formulation comprises 1% v/v of a blend comprising the EPA, the DHA, and the cholesterol.

19. The medium of claim 18, wherein the blend comprises 180 milligrams of the EPA, 120 milligrams of the DHA, and 5 milligrams of the cholesterol.

\* \* \* \* \*